United States Patent
Lee et al.

(10) Patent No.: US 11,480,567 B2
(45) Date of Patent: *Oct. 25, 2022

(54) ENHANCED SENSITIVITY AND SPECIFICITY FOR POINT-OF-CARE (POC) MICRO BIOCHIP

(71) Applicant: New Jersey Institute of Technology, Newark, NJ (US)

(72) Inventors: Eon Soo Lee, Tenafly, NJ (US); Bharath Babu Nunna, Randolph, NJ (US)

(73) Assignee: New Jersey Institute of Technology, Newark, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/471,419

(22) PCT Filed: Feb. 15, 2018

(86) PCT No.: PCT/US2018/018316
§ 371 (c)(1),
(2) Date: Jun. 19, 2019

(87) PCT Pub. No.: WO2018/152296
PCT Pub. Date: Aug. 23, 2018

(65) Prior Publication Data
US 2020/0182864 A1    Jun. 11, 2020

Related U.S. Application Data

(60) Provisional application No. 62/459,173, filed on Feb. 15, 2017, provisional application No. 62/459,240, filed on Feb. 15, 2017.

(51) Int. Cl.
*G01N 33/543* (2006.01)
*B01L 3/00* (2006.01)
(Continued)

(52) U.S. Cl.
CPC .... *G01N 33/5438* (2013.01); *B01L 3/502715* (2013.01); *B01L 3/502761* (2013.01);
(Continued)

(58) Field of Classification Search
CPC .......... G01N 33/5438; B01L 3/502715; B01L 2300/0636; B01L 2300/0819;
(Continued)

(56) References Cited

U.S. PATENT DOCUMENTS 6,319,469 B1   11/2001   Mian et al.
6,709,869 B2   3/2004    Mian et al.
(Continued)

FOREIGN PATENT DOCUMENTS

CN      1462878 A       12/2003
WO      2017223205 A1   12/2017

OTHER PUBLICATIONS

Tweedie et al., Fabrication of impedimetric sensors for label-free Point-of-Care immunoassay cardiac marker systems with passive microfluidic delivery, Proceedings of the 28th IEEE, EMBS Annual International Conference, pp. 4610-4614. (Year: 2006).*
(Continued)

*Primary Examiner* — Melanie Brown
(74) *Attorney, Agent, or Firm* — Lerner, David, Littenberg, Krumholz & Mentlik, LLP

(57) ABSTRACT

An apparatus and method to detect disease-specific antigens assists in disease diagnosis. Point-of-care (POC) micro biochip incorporates at least one hydrophilic microchannel for controlled and self-driven flow of body fluid. Metallic nano-interdigitated electrodes disposed within the channels give enhanced sensitivity detection. Microchannel controls flow and amplifies a capillary effect. Electrodes are fabricated on microchannel surface to detect biomolecular interactions. When a sample flows through microchannel, dis-
(Continued)

ease-specific antigens from the sample form antigen-antibody complex with antibodies immobilized on electrodes. Antigen-antibody interaction is detected via an electrical change in the biochip's nano circuit. Each electrode may include a different antibody to detect different antigens. Capacitance during antigen-antibody interaction without microfluidic flow is higher than with microfluidic flow due to immobilized antibodies instability on sensing surface caused by shear stress. POC biochip provides nano level detection of many disease-specific antigens of any type based on micro volume or single drop sized sample.

20 Claims, 16 Drawing Sheets

(51) Int. Cl.
G01N 27/02 (2006.01)
G01N 27/22 (2006.01)

(52) U.S. Cl.
CPC ......... *G01N 27/028* (2013.01); *G01N 27/228* (2013.01); *B01L 2300/0636* (2013.01); *B01L 2300/0645* (2013.01); *B01L 2300/0819* (2013.01); *B01L 2300/0861* (2013.01); *B01L 2300/12* (2013.01); *B01L 2300/161* (2013.01); *B01L 2400/0406* (2013.01)

(58) Field of Classification Search
CPC ..... B01L 2300/0645; B01L 2300/0861; B01L 2300/12; B01L 2300/161; B01L 2400/0406
See application file for complete search history.

(56) References Cited

U.S. PATENT DOCUMENTS

| | | | |
|---|---|---|---|
| 7,087,148 B1 | 8/2006 | Blackburn et al. | |
| 7,179,421 B1* | 2/2007 | Ho | G01N 27/126 422/50 |
| 8,354,307 B2 | 1/2013 | Lee | |
| 9,234,867 B2 | 1/2016 | Briman et al. | |
| 9,897,608 B2 | 2/2018 | Huang et al. | |
| 10,481,154 B2 | 11/2019 | Lee et al. | |
| 2005/0084921 A1 | 4/2005 | Cranley et al. | |
| 2005/0095698 A1 | 5/2005 | Carlson | |
| 2005/0100937 A1 | 5/2005 | Holmes | |
| 2005/0158704 A1 | 7/2005 | Tyvoll et al. | |
| 2006/0147344 A1 | 7/2006 | Ahn et al. | |
| 2006/0193748 A1 | 8/2006 | Tai et al. | |
| 2007/0116701 A1 | 5/2007 | Gurney et al. | |
| 2007/0122819 A1* | 5/2007 | Wu | G01N 33/54373 435/6.11 |
| 2007/0269883 A1* | 11/2007 | Uhrich | B82Y 40/00 435/287.2 |
| 2008/0253929 A1 | 10/2008 | Park et al. | |
| 2009/0084686 A1 | 4/2009 | Yun et al. | |
| 2010/0075340 A1 | 3/2010 | Javanmard et al. | |
| 2010/0267162 A1* | 10/2010 | Kartalov | B01L 3/502753 436/149 |
| 2010/0273672 A1* | 10/2010 | Demoustier-Champagne | G01N 33/54373 506/9 |
| 2011/0005932 A1 | 1/2011 | Jovanovich et al. | |
| 2012/0156688 A1* | 6/2012 | McAlpine | G01N 27/126 435/7.1 |
| 2013/0108801 A1* | 5/2013 | Naessens | B01L 3/50273 427/535 |
| 2014/0257047 A1 | 9/2014 | Sillay et al. | |
| 2015/0285808 A1* | 10/2015 | Nagrath | B01L 3/502761 435/7.23 |
| 2016/0099701 A1 | 4/2016 | Rinaldi et al. | |
| 2016/0169905 A1 | 6/2016 | Verschoor et al. | |
| 2016/0299138 A1* | 10/2016 | Almasri | B01L 3/502761 |
| 2016/0303565 A1 | 10/2016 | Bhagat et al. | |
| 2016/0318018 A1* | 11/2016 | Hsiung | B01L 3/502753 |
| 2017/0067889 A1 | 3/2017 | Tamir | |
| 2018/0128823 A1 | 5/2018 | Lee et al. | |
| 2018/0303386 A1 | 10/2018 | Hall et al. | |

OTHER PUBLICATIONS

Guest Commentary, Definitions for Hydrophilicity, Hydrophobicity and Superhydrophobocity: Getting the Basics Right, The Journal of Physical Chemistry Letters, pp. 686-688. (Year: 2014).*
"Technical Program for Monday, Nov. 9, 2015", NIH-IEEE 2015 Strategic Conference on Healthcare Innovations and Point-of-Care Technologies for Precision Medicine, Nov. 9-10, 2015, NIAID Conference Center, Bethesda, MD, 8 pages.
Alcantar et al., "Polyethylene glycol-coated biocompatible surfaces", Journal of Biomedical Materials Research, Jun. 2000, pp. 343-451.
Altintas et al., "A novel magnetic particle-modified electrochemical sensor for immunosensor applications", Sensors and Actuators B: Chemical, vol. 174, Nov. 2012, pp. 187-194.
Altintas et al., "Gold nanoparticle modified capacitive sensor platform for multiple marker detection", Talanta, vol. 118, Jan. 2014, pp. 270-276.
American Cancer Society, Cancer Facts & Figures 2017, Atlanta: American Cancer Society, 2017, pp. 1-76.
American Cancer Society, Survival Rates for Ovarian Cancer, American Cancer Society 2019, pp. 1-5.
Ayliffe et al., "Electric Impedance Spectroscopy Using Microchannels With Integrated Metal Electrodes", IEEE Journal of Microelectromechanical Systems, vol. 8, No. 1, Mar. 1999, pp. 50-57.
Balasubramanian, et al. "Biosensors based on carbon nanotubes", Analytical and Bioanalytical Chemistry, vol. 385, Issue 3, Jun. 2006, pp. 452-468.
Buys et al., "Effect of Screening on Ovarian Cancer Mortality: The Prostate, Lung, Colorectal and Ovarian (PLCO) Cancer Screening Randomized Controlled Trial", Journal of American Medical Association, vol. 305, No. 22, Jun. 2011, pp. 2295-2303.
Calonge, Ned, "Screening for Ovarian Cancer: Recommendation Statement", Annals of Family Medicine, vol. 2, No. 3, May/Jun. 2004, pp. 260-262.
Chang et al., "Trace analysis of androgens and progestagens in environmental waters by ultra-performance liquid chromatography-electrospray tandem mass spectrometry", Journal of Chromatography A, vol. 1195, Apr. 2008, pp. 44-51.
Cramer et al., "Ovarian Cancer Biomarker Performance in Prostate, Lung, Colorectal, and Ovarian Cancer Screening Trial Specimens", American Association for Cancer Research, Mar. 2011, pp. 365-375.
Das et al., "Protein Detection Using Arrayed Microsensor Chips: Tuning Sensor Footprint to Achieve Ultrasensitive Readout of CA-125 in Serum and Whole Blood", American Chemical Society, Analytical Chemistry, vol. 83, Jan. 18, 2011, pp. 1167-1172.
Diehl et al., "Hodgkin Lymphoma", Hematol Oncol Clin N Am 28 (2014) ix-x, Feb. 2014, pp. 1-2.
Gabriel et al., "The dielectric properties of biological tissues: I. Literature survey", Physics in Medicine & Biology, vol. 11, No. 11, Apr. 1996, pp. 2231-2249.
Gohagan et al., "The Prostate, Lung, Colorectal and Ovarian (PLCO) Cancer Screening Trial of the National Cancer Institute: History, Organization, and Status", Controlled Clinical Trials, vol. 21, Issue 6, Supplemental 1, Dec. 2000, pp. 251S-272S.
Gómez-Sjöberg et al., "Impedance Microbiology-on-a-Chip: Microfluidic Bioprocessor for Rapid Detection of Bacterial Metabolism", Journal of Microelectromechanical Systems, vol. 14, No. 4, Aug. 2005, pp. 829-838.
Grossman, David; "Screening for Ovarian Cancer US Preventive Services Task Force Recommendation Statement", Clinical Review & Education, American Medical Association, vol. 319, No. 6, Feb. 13, 2018, pp. 588-594.

(56) References Cited

OTHER PUBLICATIONS

Jacobs et al., "Review: Carbon nanotube based electrochemical sensors for biomolecules", Analytica Chimica Acta, vol. 662, Mar. 2010, pp. 105-127.
Jiang et al., "Gold-Labeled Nanoparticle-Based Immunoresonance Scattering Spectral Assay for Trace Apolipoprotein AI and Apolipoprotein B", Clinical Chemistry, vol. 52, No. 7, Jun. 2006, pp. 1389-1394.
Jiang et al., "Protein immobilization on carbon nanotubes via a two-step process of diimide-activated amidation", Journal of Materials Chemistry, vol. 14, Nov. 2003, pp. 37-39.
Jokerst, et al., "Nano-Bio-Chips for High Performance Multiplexed Protein Detection: Determinations of Cancer Biomarkers in Serum and Saliva Using Quantum Dot Bioconjugate Labels", Biosensors and Bioelectronics, vol. 24, No. 12, Aug. 2009, pp. 3622-3629.
Kozak et al., "Characterization of serum biomarkers for detection of early stage ovarian cancer", Proteomics, vol. 5, Mar. 2005, pp. 4589-4596.
Kramer et al., "A National Cancer Institute Sponsored Screening Trial for Prostatic, Lung, Colorectal, and Ovarian Cancers", Cancer Supplement, vol. 71, No. 2, Jan. 1993, pp. 589-593.
Lab-on-a-chip technology to help protect future space explorers and detect life forms on Mars, SpaceRef. 2017. Retrieved on Mar. 7, 2017 at http://www.spaceref.com/news/viewpr.html?pid=14312.
Lu et al., "Ultrasensitive electrochemical immunosensor for HE4 based on rolling circle amplification", Biosensors and Bioelectronics, vol. 33, Jan. 16, 2012, pp. 216-221.
Mamishev et al., "Interdigital Sensors and Transducers", Proceedings of the IEEE, vol. 92, No. 5, May 2004, pp. 808-845.
Memarzadeh, Sanaz, "Five Facts About Ovarian Cancer Everyone Should Know", Newsroom, University of California, Los Angeles (UCLA), Health Sciences, Aug. 2018, 4 pages.
Mok et al., "Prostasin, a Potential Serum Marker for Ovarian Cancer: Identification Through Microarray Technology", Journal of the National Cancer Institute, vol. 93, No. 19, Oct. 3, 2001, pp. 1458-1464.
Moore, et al., "The use of multiple novel tumor biomarkers for the detection of ovarian carcinoma in patients with a pelvic mass", Gynecologic Oncology, vol. 108, Issue 2, Feb. 2008, pp. 402-408.
Munoz, Hector, "Detecting Ovarian Cancer with a Cell Phone and a Microfluidic Chip", Microfluidic Future, Oct. 2011, 8 pages.
NIH National Cancer Institute; Cancer Screening and Early Detection Research; Research Areas: Screening and Early Detection—National Cancer Institute, https://www.cancer.gov/research/areas/screening, Updated Dec. 19, 2018, pp. 1-5.
Munna et al., "Biomolecular Detection using Molecularly Imprinted Polymers (MIPs) at Point-of-Care (POC) Micro Biochip", Ovarian Cancer Diagnosis using Micro Biochip, NIH-IEEE 2015 Strategic Conference on Healthcare Innovations & Point-of-Care Technologies for Precision Medicine, (PCHT15-0056) Nov. 9-10, 2015, p. 1.
Nunna et al., "Influence on Capillary Flow of Human Blood in PDMS Micro Channels due to various Surface Treatments", Jul. 2016, Technical Presentation Only. ICNMM2016-8122, 1 page.
Nunna, et al., "Innovative Point-of-Care (POC) Micro Biochip for Early Stage Ovarian Cancer Diagnostics", Sensors & Transducers, vol. 214, No. 7, Jul. 2017, 9 pages.
Nunna, et al., "Point-of-Care (POC) Micro Biochip for Cancer Diagnostics", Id Innovation Conference and Expo 2017, May 2017, pp. 110-113.
Rusling, et al., "Measurement of Biomarker Proteins for Point-of-Care Early Detection and Monitoring of Cancer", Analyst, vol. 135, No. 10, Jul. 2010, pp. 2496-2511.
Schummer et al., "Evaluation of ovarian cancer remission markers HE4, MMP7 and Mesothelin by comparison to the established marker CA125", Gynecol Oncology, vol. 125, No. 1, Apr. 2012, pp. 1-12.
Shadfan, et al., "A Multiplexable, Microfluidic Platform for the Rapid Quantitation of a Biomarker Panel for Early Ovarian Cancer Detection at the Point-of-Care", Cancer Prevention Research, vol. 8, No. 1, Jan. 2015, 19 pages.
Siegel et al., "Colorectal Cancer Statistics, 2017", CA: A Cancer Journal for Clinicians, vol. 67, No. 3, May/Jun. 2017, pp. 177-193.
Soper et al., "Point-of-care biosensor systems for cancer diagnostics/prognostics", Biosensors and Bioelectronics, vol. 21, Issue 10, Apr. 15, 2006, pp. 1932-1942.
Su et al., "Ferrocenemonocarboxylic-HRP@Pt nanoparticles labeled RCA for multiple amplification of electro-immunosensing", Biosensors and Bioelectronics, vol. 26, May 6, 2011, pp. 4601-4604.
Tcherkassova, et al., "Combination of CA125 and RECAF biomarkers for early detection of ovarian cancer", Tumor Biology, vol. 32, May 28, 2011, pp. 831-838.
Tsouti et al., "Capacitive microsystems for biological sensing", Biosensors and Bioelectronics, vol. 27, May 2011, pp. 1 -11.
Wang et al., "Solubilization of Carbon Nanotubes by Nafion toward the Preparation of Amperometric Biosensors", Journal of American Chemical Society, vol. 125, No. 9, Feb. 2003, pp. 2408-2409.
Wang, Joseph "Electrochemical biosensors: Towards point-of-care cancer diagnostics", Biosensors and Bioelectronics, vol. 21, Issue 10, Apr. 2006, pp. 1887-1892.
Waxman, Alan; "Guidelines for Cervical Cancer Screening: History and Scientific Rationale", Clinical Obstetrics and Gynecology, vol. 48, No. 1, Mar. 2005, pp. 77-97.
Zhang, et al., "Microfluidics and Cancer: Are We There Yet?", Biomedical Microdevices, vol. 15, No. 4, Aug. 2013, pp. 595-609.
Zhu et al., "Electrochemical Determination of Reversible Redox Species at Interdigitated Array Micro/Nanoelectrodes Using Charge Injection Method", IEEE Transactions on Nanobioscience, vol. 4, No. 2, Jun. 2005, pp. 164-169.
American Cancer Society, "Cancer Facts and Figures 2016," copyrighted 2016, American cancer Society Inc., Atlanta, Ga.; 72 pages.
World Ovarian Cancer Day, About Ovarian Cancer, World Ovarian Cancer Day 2019, pp. 1-5, https://ovariancancerday.org/what-is-ovarian-cancer/.
Lazcka, et al., "Pathogen Detection: A Perspective of Traditional Methods and Biosensors", Biosensors and Bioelectronics, vol. 22, No. 7, Feb. 2007, pp. 1205-1217.
Nunna, et al., "Ovarian Cancer Diagnosis Using Micro Biochip", InNIH-IEEE 2015 Strategic Conference on Healthcare Innovations and Point-of-Care Technologies for Precision Medicine (PCHT15-0056), Nov. 2015, pp. 9-10.
Rusling, et al., "Measurement of Biomarker Proteins for Point-of-Care Early Detection and Monitoring of Cancer", Analyst, vol. 135, No. 10, Oct. 2010, pp. 2496-2511.
"Lab-on-a-chip technology to help protect future space explorers and detect life forms on Mars", SpaceRef, Press Release From: Marshall Space Flight Center (http://www.msfc.nasa.gov/), Posted: Tuesday, Jun. 1, 2004.
Lucas, R., "Rate of Capillary Ascension of Liquids", Kolloid Z, vol. 23, No. 15, 1918, pp. 15-22.
Chikawa, et al., "Interface Motion of Capillary-Driven Flow in Rectangular MicroChannel", Journal of Colloid and Interface Science, vol. 280, No. 1, Dec. 2004, pp. 155-164.
Alcantar, et al., "Polyethylene Glycol-Coated Biocompatible Surfaces", Journal of Biomedical Materials Research: An Official Journal of the Society for Biomaterials, the Japanese Society for Biomaterials, and the Australian Society for Biomaterials and the Korean Society for Biomaterials, vol. 51, No. 3, Sep. 2000, pp. 343-351.
Whitesides, George, "The Origins and the Future of Microfluidics", Nature, vol. 442, Jul. 2006, pp. 368-373.
Washburn, Edward, "The Dynamics of Capillary Flow", Physical Review, vol. 17, No. 3, Mar. 1921, pp. 273-283.
Ginn BT, Steinbock O. Polymer surface modification using microwave-oven-generated plasma. Langmuir. Sep. 16, 2003;19(19):8117-8.
Xiao D, Zhang H, Wirth M. Chemical modification of the surface of poly (dimethylsiloxane) by atom-transfer radical polymerization of acrylamide. Langmuir. Dec. 10, 2002;18(25):9971-6.
Eddington DT, Puccinelli JP, Beebe DJ. Thermal aging and reduced hydrophobic recovery of polydimethylsiloxane. Sensors and Actuators B: Chemical. Mar. 30, 2006;114(1):170-2.
Daniels et al., "Label-Free Impedance Biosensors: Opportunities and Challenges", National Institutes of Health, vol. 19, No. 12, May 16, 2007, pp. 1239-1257.

(56) References Cited

OTHER PUBLICATIONS

Zhuang et al., "Synthesis of Nitrogen-Doped Graphene Catalyst By High-Energy Wet Ball Milling for Electrochemical Systems", International Journal of Energy Research, Jun. 12, 2016, pp. 1-14.
Berggren et al., "Capacitive Biosensors", Journal of Electroanalysis, vol. 13, No. 3, Oct. 2000, pp. 173-180.
Zhuang et al., "New Nitrogen-Doped Graphene/MOF-modified catalyst for Fuel Cell Systems", The Electrochemica Society ECS Transactions, vol. 72 (8), Jun. 1, 2016, pp. 149-154.
Tsouti V, Boutopoulos C, Zergioti I, Chatzandroulis S. Capacitive microsystems for biological sensing. Biosensors and Bioelectronics. Sep. 15, 2011;27(1):1-1.
Laczka O, Baldrich E, Mun~oz FX, del Campo FJ. Detection of *Escherichia coli* and *Salmonella typhimurium* using interdigitated microelectrode capacitive immunosensors: the importance of transducer geometry. Analytical chemistry. Oct. 1, 2008;80(19):7239-47.
Yi M, Jeong KH, Lee LP. Theoretical and experimental study towards a nanogap dielectric biosensor. Biosensors and Bioelectronics. Jan. 15, 2005;20(7):1320-6.
Sarojini et al., "Early Detection Biomarkers for Ovarian Cancer", Journal of Oncology, vol. 2012, Article ID 709049, Nov. 19, 2012, pp. 1-15.
Van Gerwen P, Laureyn W, Laureys W, Huyberechts G, De Beeck MO, Baert K, Suis J, Sansen W, Jacobs P, Hermans L, Mertens R. Nanoscaled interdigitated electrode arrays for biochemical sensors. Sensors and Actuators B: Chemical. Jun. 25, 1998;49(1-2):73-80.
Kallempudi et al., "A nanostructured-nickel based interdigitated capacitive transducer for biosensor applications", Sensors and Actuators B: Chemical, vol. 160, Issue 1, Dec. 2011, pp. 891-898.
Carrara S, Bhalla V, Stagni C, Benini L, Ferretti A, Valle F, Gallotta A, Riccò B, Samorì B. Label-free cancer markers detection by capacitance biochip. Sensors and Actuators B: Chemical. Feb. 2, 2009;136(1):163-72.
Limbut W, Kanatharana P, Mattiasson B, Asawatreratanakul P, Thavarungkul P. A comparative study of capacitive immunosensors based on self-assembled monolayers formed from thiourea, thioctic acid, and 3-mercaptopropionic acid. Biosensors and Bioelectronics. Aug. 15, 2006;22(2):233-40.
Lamour G, Hamraoui A, Buvailo A, Xing Y, Keuleyan S, Prakash V, Eftekhari-Bafrooei A, Borguet E. Contact angle measurements using a simplified experimental setup. Journal of chemical education. Dec. 1, 2010;87(12):1403-7.
Hrncír E, Rosina J. Surface tension of blood. Physiol Res. Jan. 1997;46:319-21.
Nunna et al., "Flow control mechanism of capillary driven flow in microchannel using non-mechanical forces", Bulletin of the American Physical Society, APS—69th Annual Meeting of the APS Division of Fluid Dynamics—Session Index DFD16, Nov. 2016, pp. 1-2 (Abstract Only included).
Nunna BB, Zhuang S, Lee ES. Squeeze flow with capillary effect in Nano Imprint Lithography (NIL) process. APS. Nov. 2015:M1-004.
Nunna BB, Zhuang S, Lee ES. Hemorheology in PDMS micro channel with varied surface roughness. APS. Nov. 2015:KP1-116.
Tan SH, Nguyen NT, Chua YC, Kang TG. Oxygen plasma treatment for reducing hydrophobicity of a sealed polydimethylsiloxane microchannel. Biomicrofluidics. Sep. 30, 2010;4(3):032204.
Dimaki et al., "A Compact Microelectrode Array Chip With Multiple Measuring Sites For Electrochemical Applications", Sensors (Basel), May 2014, vol. 14 No. 6, pp. 9505-9521.
International Application Status Report for Application No. PCT/US2018/018316 dated Mar. 1, 2018, 2 pages.
International Search Report from Application No. PCT/US2018/018316 dated Jun. 15, 2018, 2 pages.
Nunna, Bharath et al., "Biomolecular Detection using Molecularly Imprinted Polymers (MIPs) at Point-of-Care (POC) Micro Biochip," Conference Paper, Nov. 2016, ResearchGate, https://www.researchgate.net/piblication/312191507, 2 pages.

\* cited by examiner

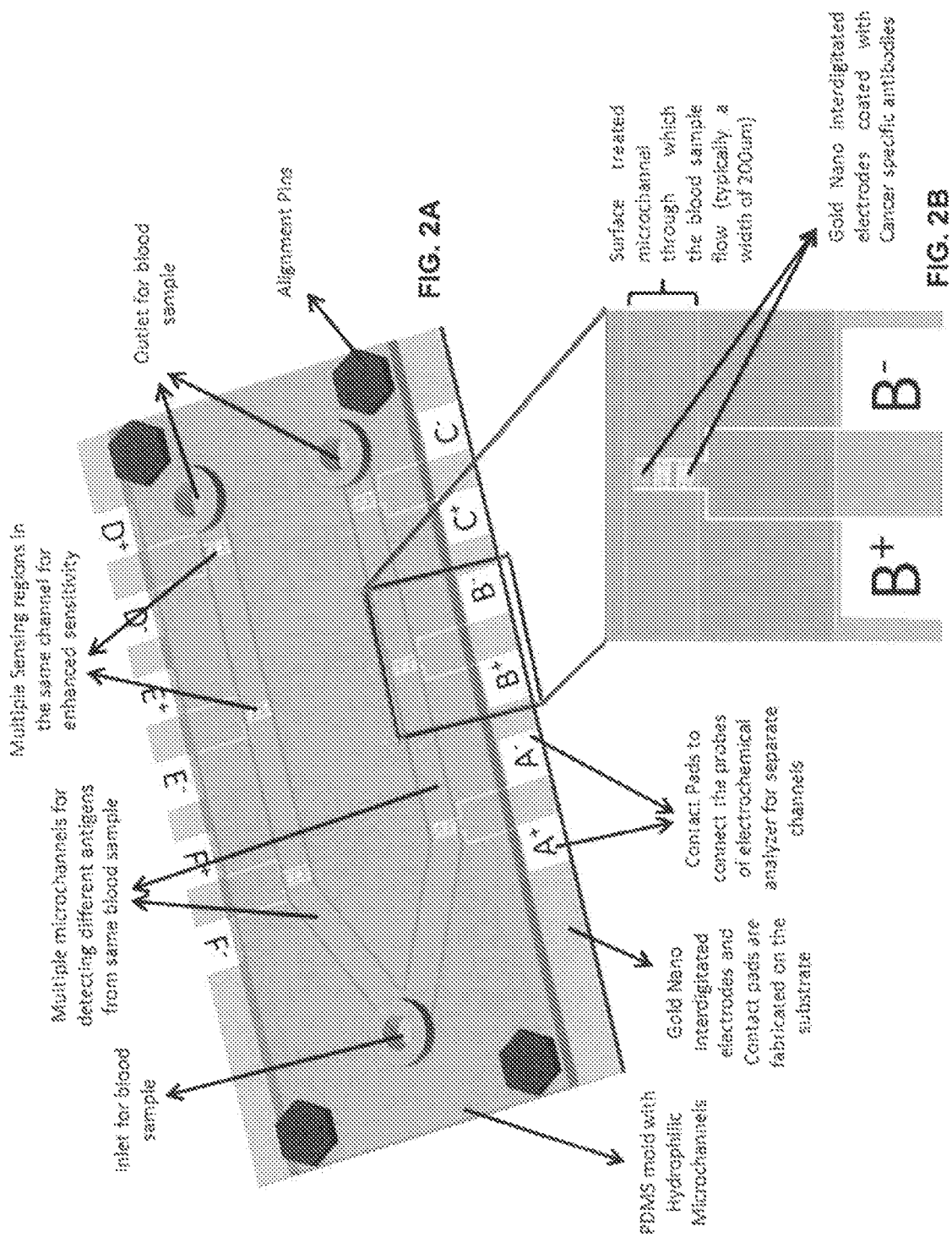

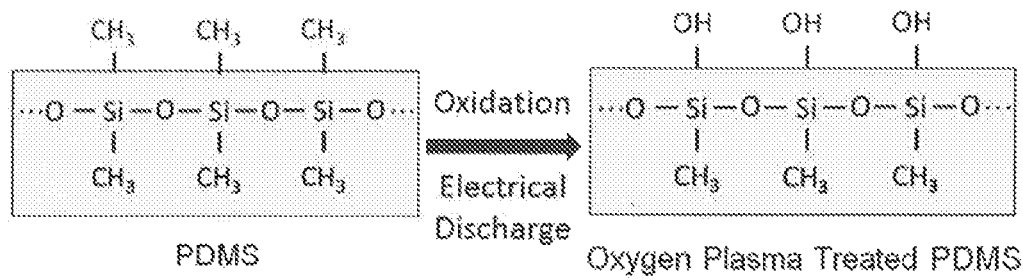
FIG. 6
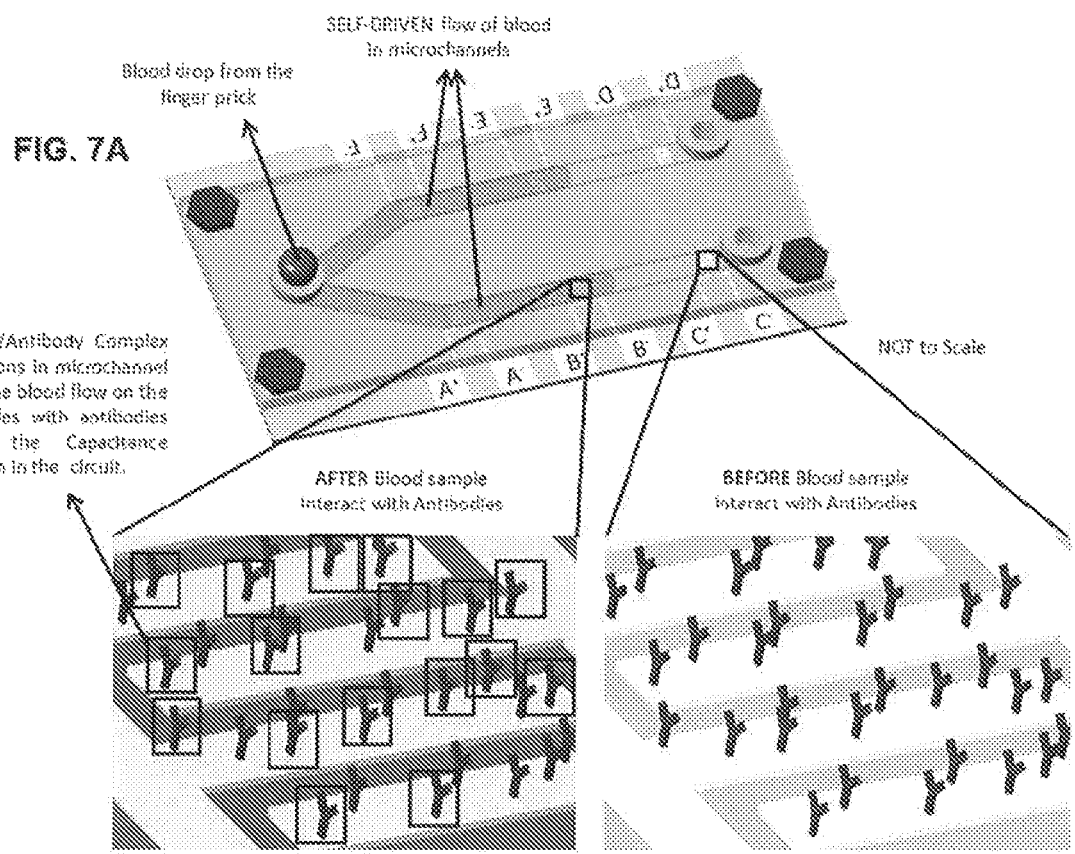
FIG. 7A
FIG. 7B
FIG. 7C

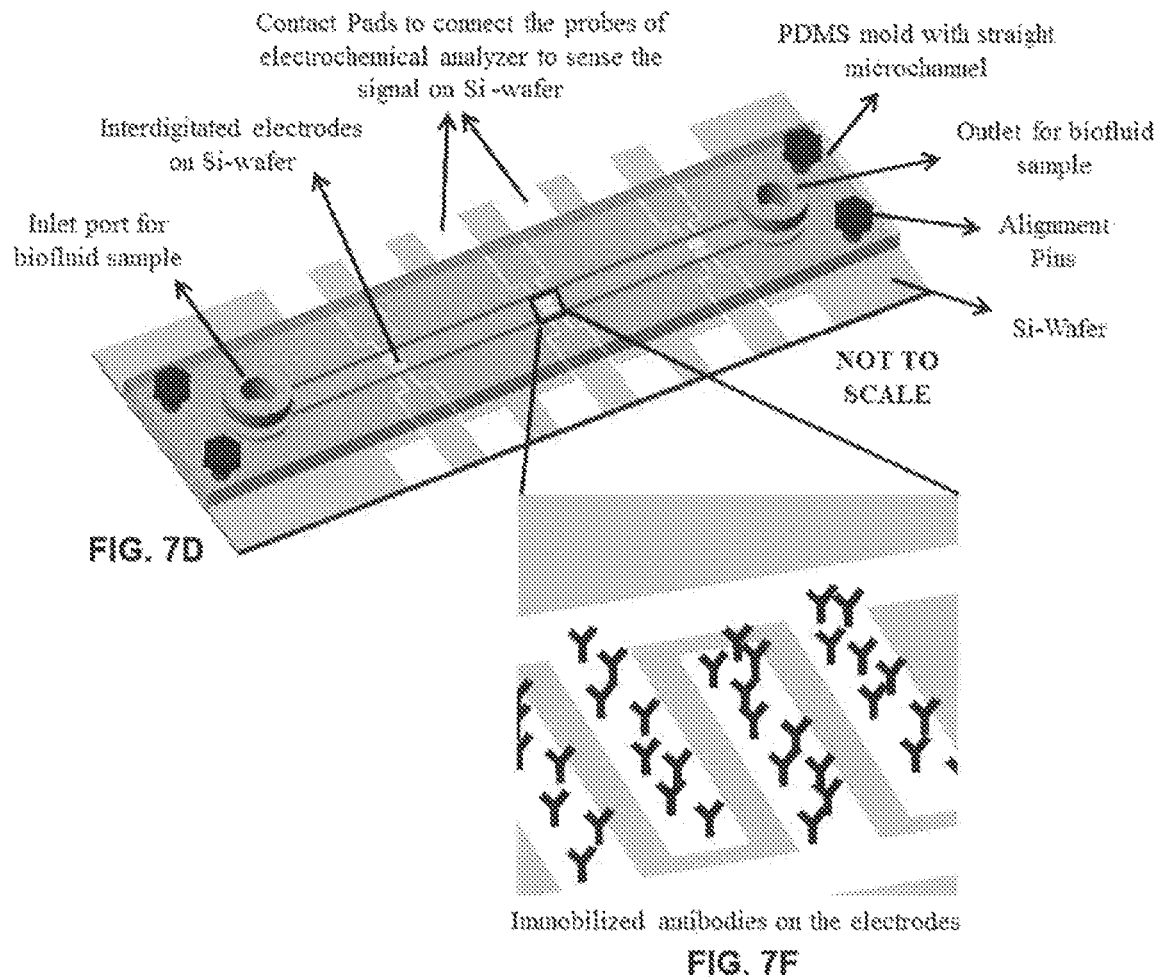
FIG. 7D
Immobilized antibodies on the electrodes
FIG. 7F
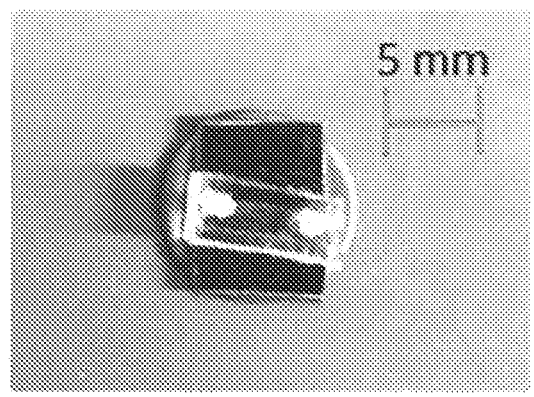
Biosensor with PDMS microchannel
FIG. 7E

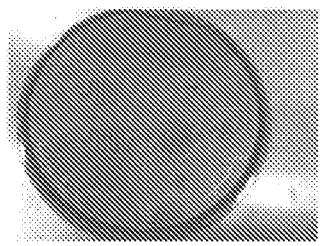
FIG. 11A
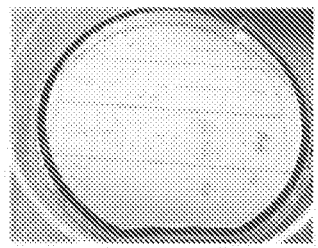
FIG. 11B
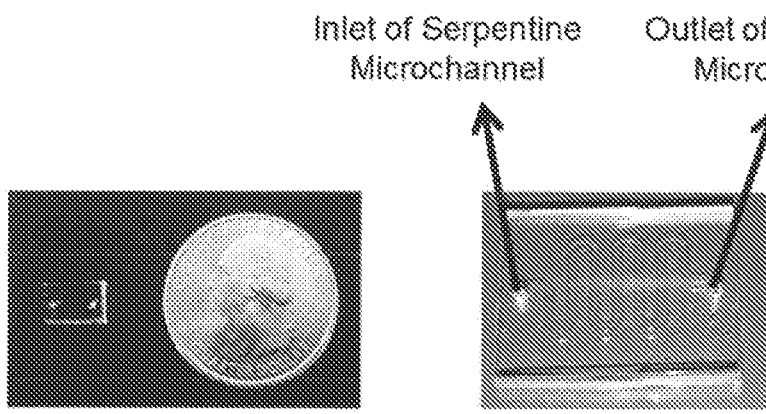
FIG. 12A  FIG. 12B
Si wafer with Micro channels
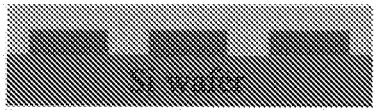
Fabrication of PDMS Slab
PDMS mold with microchannels
Punching the inlet and outlet ports
Binding to Si wafer with Gold IDE
FIG. 13

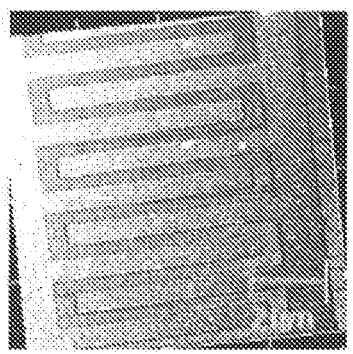 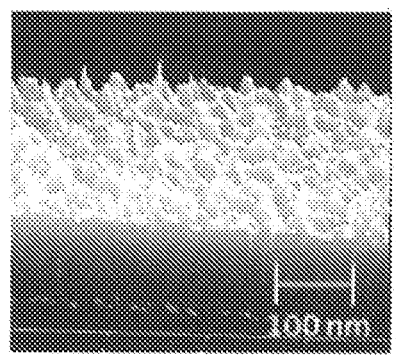 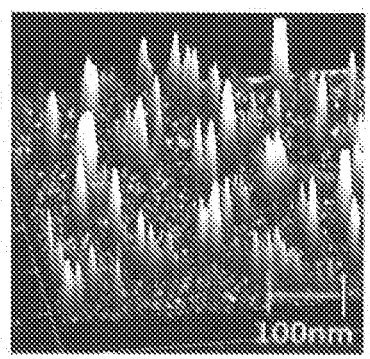
FIG. 17A  FIG. 17B  FIG. 17C
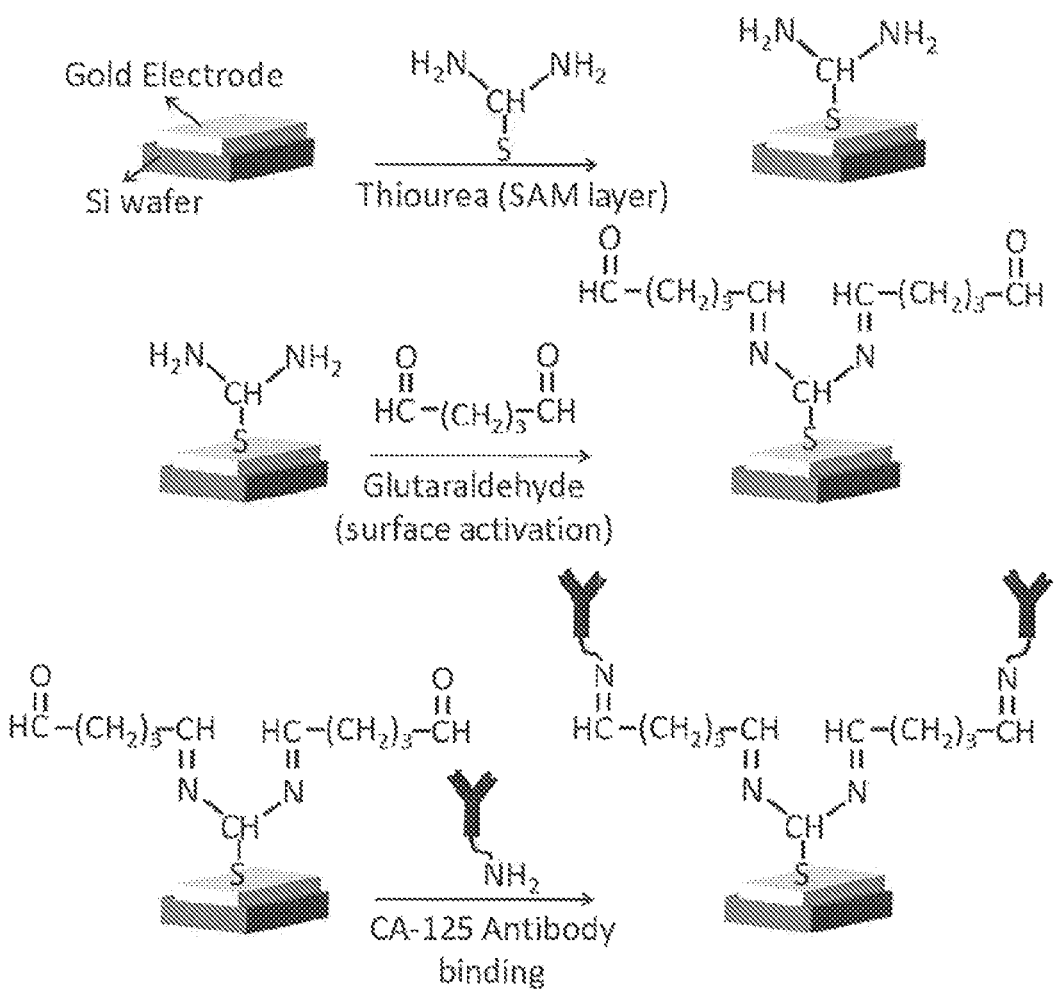
FIG. 18A

ENHANCED SENSITIVITY AND SPECIFICITY FOR POINT-OF-CARE (POC) MICRO BIOCHIP

CROSS-REFERENCE TO RELATED APPLICATION

The present application is a national entry under 35 U.S.C. § 371 of Internation Application No. PCT/US2018/0183316, filed Feb. 15, 2018, which claims the benefit of the filing date of U.S. Provisional Patent Application No. 62/459,173, filed Feb. 15, 2017, and U.S. Provisional Patent Application No. 62/459,240, also filed Feb. 15, 2017, the disclosures of both are hereby incorporated herein by reference.

TECHNICAL FIELD

This invention relates to an apparatus and method of preparing a point-of-care micro biochip for disease diagnostics. More particularly, it relates to a novel apparatus and way to increase sensitivity and specificity of antigen test readings from a single sample source.

BACKGROUND

Early detection of diseases can, among other thing, enhance preventive measures, increase curability of the disease, reduce health care costs, and improve the quality of life for patients. Most diseases, like some forms of cancer, are curable when they are detected at earlier stages. For example, ovarian cancer, a complex disease, has significant variation in the survival rate depending on the stage at which the disease is diagnosed. With the current prevailing technologies, 85% of ovarian cancer cases are detected at advanced stages, at which the survival rate is 31%. However, only 15% of the ovarian cancer cases are detected at early stages, for example stages 1A & 1B, at which the survival rate is much higher at 93%.

There is a need in the art to allow the disease diagnosis process to become easier and more available to patients. Such access would lead to more frequent self-evaluations in which patients would have a much higher chance of having an earlier diagnosis. Early detection can help to enhance treatment outcomes.

However, current conventional diagnosis processes are inefficient and lack the detection sensitivity needed for early diagnosis. For example current techniques lack the continuous monitoring of the disease and treatment. A patent must submit to lab testing that may take several days to complete. Furthermore, current testing mostly contains standard test biomarkers and lacks the ability to personalize testing for each patient. Current state of the art testing lacks the ability to efficiently detect several biomarkers and lacks the capability to offer a varied biosensor array for personalized therapies.

Biochips hold promising results for early diagnosis. Biochips are defined as devices on which biomolecules such as DNA, proteins, sugar chains and cells containing these biomolecules are fixed in a large number, termed DNA, protein, glycochips and cell chips, respectively. Target molecules and compounds may interact with biomolecules on these chips that when analyzed may detect a disease state.

However current state of the art biochips have many drawbacks. For example, diagnosis including screening and monitoring in the early phase after onset is difficult with current health check-up sensitivity and specificity. There is still a need to detect diseases such as cancers, lifestyle-related diseases such as hypertension and diabetes, and infectious diseases including influenza rapidly, simply and accurately at a low cost using one drop of blood or test sample. Furthermore some biochips lack the ability to utilize other patient samples other than blood, for example other bodily fluids such as urine, saliva, spinal fluid, and the like. Also some biochips are manufactured with glass that causes problems due to etching of the glass, cost of manufacturing, and extreme limitation of biochip construction. Use of other materials such as polymer based materials has failed due to the hydrophobic nature of the polymer material and its tendency for reducing the flow of any fluid.

Thus there still remains a need for an easy to use diagnostic device and method that may be used in the doctor's office, hospital, laboratory, or home settings without the above drawbacks. Furthermore there also remains a need in the art for a diagnostic device or method that utilizes a single patient sample and enhances sensitivity and/or specificity of disease detection.

There is still a need to detect diseases such as cancers, lifestyle-related diseases such as hypertension and diabetes, and infectious diseases including influenza, rapidly, simply and accurately at a low cost using one drop of blood or test sample. Furthermore some biochips lack the ability to utilize other patient samples other than blood, for example other bodily fluids such as urine, saliva, spinal fluid, and the like. Also, some biochips are manufactured with glass that causes problems due to etching of the glass, cost of manufacturing, and extreme limitation of biochip construction. Use of other materials such as polymer based materials has failed due to the hydrophobic nature of the polymer material and its tendency for reducing the flow of any fluid.

In addition, although biochip technology holds great potential for use in health monitoring systems around the world, and in particular in remote areas, there remain significant areas for improvement in the performance and ease of use of such technology. Complex disease diagnostics such as cancer diagnostics is still a nascent area of research that has not been completely explored by biochip researchers. Further improvement through study and development in this area would be desirable.

SUMMARY OF THE INVENTION

The present invention solves the problems of current state of the art and provides many more benefits. Disclosed is a point-of-care (POC) micro biochip that may be used to diagnose complex diseases, like cancer, in the doctor office, hospital, laboratory or even home settings. The (POC) micro biochip incorporates a controlled self-driven flow of the bio fluid such as, but not limited to, blood onto gold or similar metallic conductive material, nano interdigitated electrodes to sense biomolecular reactions in nano and femto levels. Such metallic materials may include, but are not limited to, silver, gold, platinum or other conductive metals. The nano interdigitated electrodes contain an immobilized biomarker specific to the disease desired to be identified. The biomarker is any measurable substance in an organism whose presence is indicative of some phenomenon such as disease, infection, or environmental exposure. An antigen, for example, would react within the sample creating an antigen-antibody complex formation that affects the electrical properties of the biochip circuit. Such electrical properties include, but are not limited to, capacitance, impedance, voltage and any combination thereof.

The biochip device and method are versatile and cost effective. Poly(dimethylsiloxane) (PDMS) may be utilized as well as any 3D printer material or polymeric material to construct hydrophilic microchannels. The microchannels may be manufactured using any 3D printer that increases the number of channel configurations available for the biochip. In addition, the PDMS or other 3D printer material is treated either by plasma treatment or other wetting treatments to increase the hydrophilicity of the material. The microchannels provide self-driven flow of the sample due to a capillary action in the microchannels. Various designs of the microchannels may be manufactured to increase the capillary effect of the flow of the sample.

A single sample source such as a drop of blood is only required for the biochip diagnostic testing. The bio fluid may include, but is not limited to, tissue (dissolved in solution), blood, spinal fluid, saliva, urine and the like. Detection is easy to use and enhances sensitivity and/or specificity of disease detection.

Increasing the amount of nano interdigitated electrodes in the at least one microchannel to sense biomolecular reactions in nano and femto levels will increase the sensitivity of the biochip to detect or monitor a disease state. The number of channels may also be increased to increase sensitivity; however, only at least one microchannel is required for the device and method. Furthermore, various biomarkers may be included in the micro channel and/or in other micro channels to increase the selectivity of what disease state is being detected. Thus several diseases may be identified on one biochip. Also, the selection of what the biochip is detecting may be easily configured.

The surface treatment of the microchannels, for example PDMS microchannels, helps in controlling the contact angle from a range of 107.12° to 47.07°. The self-driven flow in microchannel is controlled by altering the contact angle. The controlled flow rate in microchannels helps to provide necessary conditions in microchannels for biological reactions like antigen/antibody complex formation. Antibodies such as CA-125 are immobilized on the nano interdigitated electrodes, for example, gold electrodes, using thiourea and glutaraldehyde. The nano scale capacitance variation is detected in POC micro biochip when the sample is self-driven on the gold nano interdigitated electrodes coated with CA-125 antibodies, for example, due to antigen/antibody complex formation with the cancer antigens CA-125 in the sample. The POC micro biochip provides the information on existence of specific disease antigens (cancer antigens) in the blood sample from a finger prick. This information helps physicians to suggest the patient for next level of cancer diagnosis. The invention may also assist in developing new POC devices with non-optical sensing mechanisms like electrical sensing with no need for micro pumps to inject the sample.

Flow of a sample in the microchannel is self-driven due to the capillary effect of the sample in the hydrophilic microchannel. The microchannel is designed to control the flow mechanism and amplify the capillary effect of the sample flow. Gold nano interdigitated electrodes are fabricated on the surface of the microchannel to detect the biomolecular interactions in the microchannel. When the sample flows through the microchannel, the disease-specific antigens from the blood form an antigen-antibody complex with the antibodies that are immobilized on the electrodes as the sample reaches the electrodes. This antigen-antibody interaction is detected via the change in an electrical property, such as capacitance, of the nano circuit incorporated in the biochip. These experimental results provide evidence of the detection of disease-specific antigens (e.g., CA-125) using the biochip based on a micro volume of a sample, such as a blood drop from a finger prick or other body fluid.

In another embodiment, it was found that when the biofluid sample (disease antigens with phosphate buffer saline solution) was passed on the corresponding antibodies that are immobilized on the gold interdigitated electrodes, the capacitance variation of the sensing circuit was caused due to the antigen antibody interaction. However, the capacitance measured during antigen-antibody interaction with the microfluidic flow condition (270.34 pF) was lower than 'without microfluidic flow' condition (296.09 pF) due to the instability of the immobilized antibodies on the sensing surface, that was caused by the shear stress during the microfluidic flow.

Furthermore, the sensitivity variation in the device due to microfluidic flow was established by detecting antigens from the biofluid using gold interdigitated electrodes. Based on the measured results, the functionality of the individual layers in the sensing platform was validated with changes in capacitance measurements. The detection of the antigens from the biofluid sample using the interdigitated electrodes in the microfluidic flow condition was verified. The capacitive sensitivity of the biosensor 'with microfluidic flow' condition again was found lower than 'without microfluidic flow' condition due to shear stress within the micro channels of the device.

The above objects and advantages are met by the present invention. In addition the above and yet other objects and advantages of the present invention will become apparent from the hereinafter-set forth Brief Description of the Drawings, Detailed Description of the Invention and claims appended herewith. These features and other features are described and shown in the following drawings and detailed description.

BRIEF DESCRIPTION OF THE DRAWINGS

So that those having ordinary skill in the art will have a better understanding of how to make and use the disclosed device and method, reference is made to the accompanying figures wherein:

FIGS. 2A-2B are schematics of a POC micro biochip with microchannels and nano interdigitated electrodes;

FIG. 6 illustrates a schematic with oxygen plasma treatment to PDMS surface;

FIG. 7A illustrates a schematic of POC micro biochip functionality during the blood sample flow in microchannels;

FIG. 7B is an enlarged view of a portion of FIG. 7A shown after a blood sample interacts with antibodies;

FIG. 7C is an enlarged view of another portion of FIG. 7A shown before a blood sample interacts with antibodies;

FIG. 7D an image of a biosensor with a microfluidic setup;

FIG. 7E a schematic of a microfluidic flow setup on a sensing surface;

FIG. 7F a schematic of immobilized antibodies on interdigitated electrodes;

FIGS. 11A and 11B illustrate Si wafers, FIG. 11A illustrates a Si wafer after the photolithography process (channels formed from photo resist) and FIG. 11B illustrates a Si wafer after the dry etching process with microchannels of height 107 um;

FIGS. 12A and 12B illustrate a micro biochip, FIG. 12A illustrates a micro biochip size comparison and FIG. 12B illustrates a microchannel in the biochip fabricated with PDMS using photo-lithographic technique;

FIG. 13 illustrates a schematic of PDMS molds fabrication process using Si wafer with microchannel structures;

FIG. 17A illustrates an Atomic Force Microscopic (AFM) image of the gold interdigitated electrodes fabricated on the Si wafer in FIG. 16A;

FIG. 17B illustrates AFM images of the surface of the interdigitated electrodes with Bare electrodes in the SAM layer;

FIG. 17C illustrates AFM images of the surface of the interdigitated electrodes with Bare electrodes showing immobilized antibodies;

FIG. 18A illustrates a chemotic representation of CA-125 antibody immobilization on nano gold interdigitated electrodes;

DETAILED DESCRIPTION

In general, the invention overcomes the disadvantages of past attempts to detect disease-specific antigens. The invention's device and method for point-of-care (POC) micro biochip incorporates at least one hydrophilic microchannel for controlled and self-driven flow of a patient's bodily fluid. Blood is given below as merely an example of bodily fluid and in no means is meant to limit the scope of the invention. The invention may be utilized with any bodily fluid such as, but not limited to, spinal fluid, saliva, blood, urine, tissue (in solution) and any combination thereof. Multiple metallic nano interdigitated electrodes disposed within the channels give enhanced sensitivity detection. The present invention functions and utilizes one or more of the following features as shown in the below examples and below detailed description.

Figure 1A:
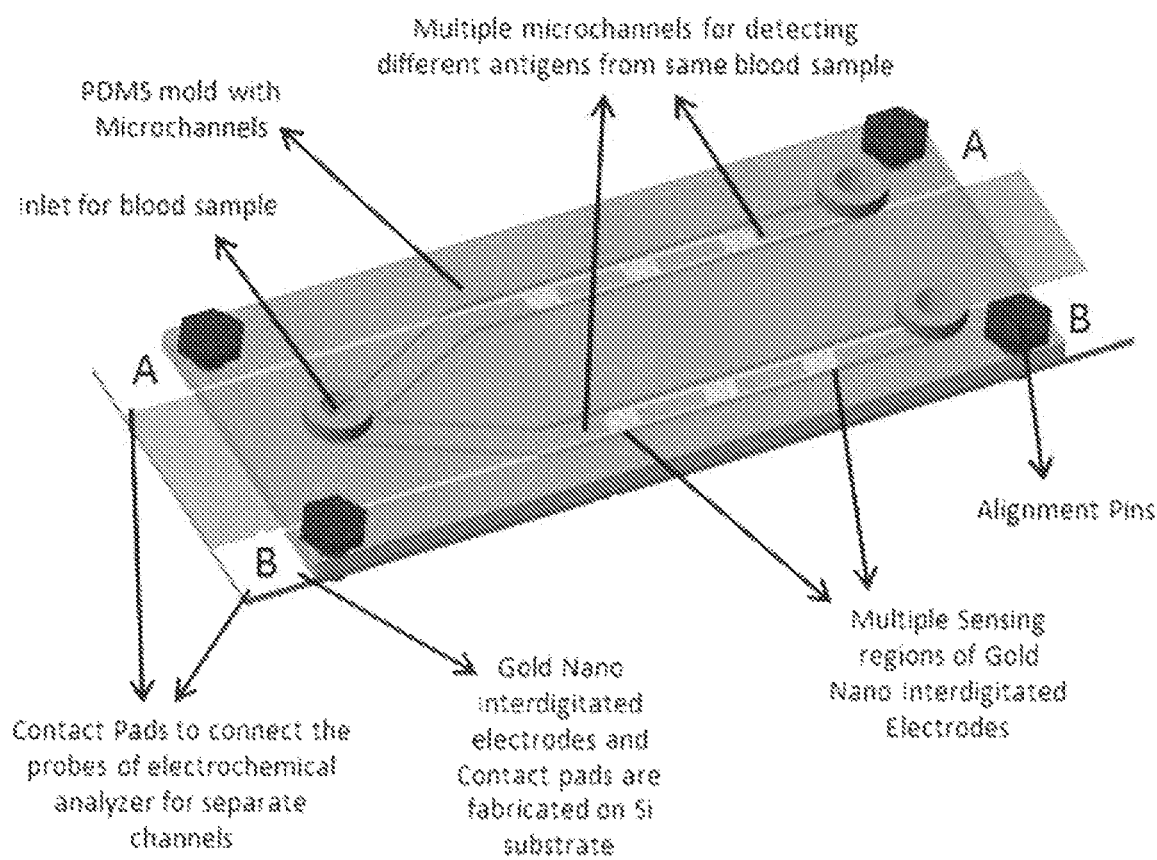
FIG. 1A is a schematic of a POC micro biochip of the present invention and FIG. 1B is a schematic of a POC micro biochip with a spiral microchannel of the present invention.
Figure 1B:
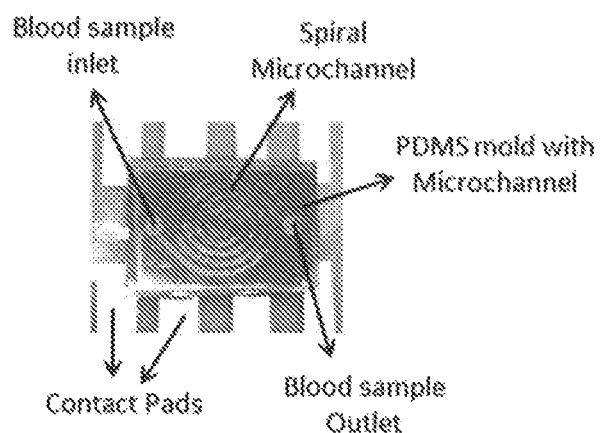

In the present invention, a POC micro biochip incorporates at least one hydrophilic microchannel to have a bodily fluid sample, such as but not limited to blood, flow without any need of external devices and electrical sensing, such as but not limited to capacitance, mechanism with nano interdigitated electrodes on the surface of the microchannel or microchannels to detect an antigen (Ag)-antibody (AB) complex formation, as shown in FIGS. 1A-1B and FIGS. 2A-2B. As shown in FIG. 1B, the microchannel does not need to be linear as shown in FIG. 1A and may be configured in various geometrical shapes. Shown in FIG. 1B is a spiral shape. The use of a 3D printer assists in making various shapes. Using glass, for example, would limit the geometrical shapes due to complex etching manufacturing and costly techniques needed to make such designs.

The spiral shape, for example, due to a centrifuge effect may be very advantageous. For example, when the bodily fluid sample is blood, plasma is separated from the blood due to the centrifuge effect of the spiral design. Also the spiral design allows different concentrations of the bodily fluid at each section. Various shapes and designs may be incorporated in the present invention to allow various benefits in the detection process.

The biochip is designed with one or multiple channels that are connected to the same inlet through which the sample flows, so as to provide feasibility of detecting different disease antigens from the same sample at the same time. Depending on the embodiment, multiple biomarker embedded or coated electrodes may have the same or different biomarkers. If one or more channels have the same biomarker, the sensitivity of detection is increased. In the POC biochip, a gold nano interdigitated electrodes (IDE), for example, may be fabricated at different sections of the microchannel to sense the biological reactions at multiple locations of microchannel, in order to multiply the sensing mechanism and enhance the detection sensitivity. The gold nano IDEs are connected to individual contact pads so that the signal from each IDE can be separately monitored. A specific antibody can be immobilized at a specific IDE so that the concentration of the corresponding antigens can be detected by the antigen-antibody complex formed at that IDE. Detection of concentration of each individual antigen in the sample can enhance the detection specificity. The conceptual details of the self-driven flow in the microchannel and the electrical property, such as capacitance, sensing mechanism in biochip are explained in the sections below.

FIGS. 2A and 2B are an example of a POC biochip fabricated and utilized to generate results for different antigens from the same sample. Multiple Nano interdigitated electrodes (IDE), for example, of the same or different biomarkers may be fabricated at different sections of the microchannel to sense the biological reactions at multiple locations of microchannel or different microchannels. Thus increased sensitivity is possible with the present invention whether the biochip is detecting one antigen, or multiple antigens from the same biochip and same one sample.

Capillary phenomena are well known in the art. Indeed, applications of capillary flow have been emerging since the early 1980s such as in lab-on-a-chip technology, inkjet propulsion, and the like. However, such use has not been seen in biochip technology due to the difficulty of manufacturing biochips with the necessary configurations to cause a capillary effect. Utilizing capillary driven flow instead of a micro-pump in the present invention minimizes the complexity of the microfluidic assembly and also reduces costs significantly.

The biochip of the present invention incorporates microchannels in order to serve two primary criteria: 1. to enhance the interaction between bio fluid (such as blood) and the sensing mechanism with high surface area to volume ratio. 2. To incorporate the self-driven flow in the microchannel without any external devices-no micro pumps needed with the present invention.

Minimizing the external device requirement for flow generation in the microchannel helps to reduce high sample volume (from milliliter to microliter) requirements and reduces the contamination of the blood sample. When a blood drop comes in contact with the micro capillary channel, the surface tension of the blood draws the drop into the microchannel and induces the fluid into motion. The capillary flow is generated due to characteristics of the surface of the microchannel and its interaction with the fluid. Capillary action is the result of both adhesion force (between the fluid and the walls of channel) and surface tension of the fluid. Surface tension is the tensile force attained by the interface due to the imbalance of the cohesive forces of the molecules on the interface and the inner molecules of the fluid. The adhesion force (attraction force between the solid and liquid molecules) of blood with the surface of the microchannel causes the forward force at the edges. The surface tension will hold the surface intact and induce the whole liquid surface to move forward instead of moving only at the edges. The surface tension quantifies the capillary phenomena.

The influence of surface tension of the bio fluid (blood) on the capillary flow depends on the contact angle. In layman's terms, the contact angle is the angle that liquid creates with a solid surface, when the liquid and the solid surfaces come in contact. The internal balance of the cohesive forces (such as hydrogen bonds and Van der Waals forces) of liquid molecules and the adhesive forces (mechanical and electrostatic forces) of liquid and solid molecules, will define the contact angle created between the solid and liquid interfaces.

Figure 2C:
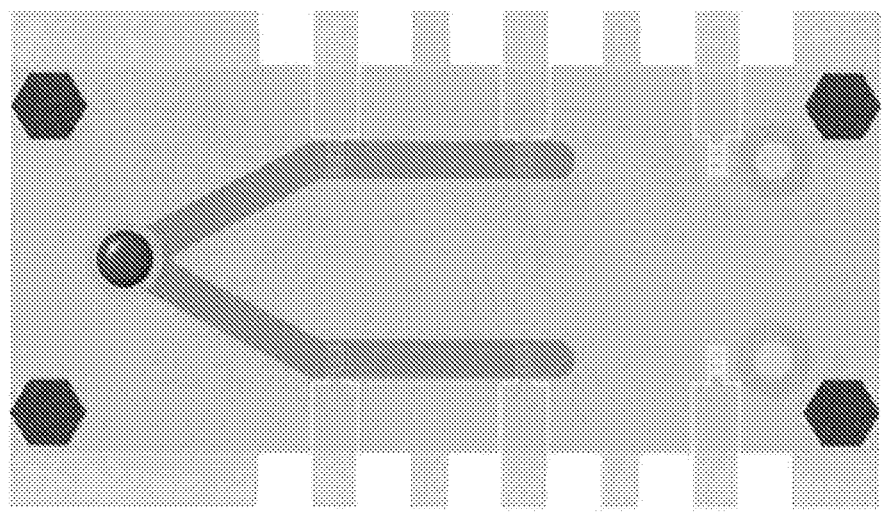
FIG. 2C illustrates a top view of the biochip of FIG. 1A.

One embodiment of the biochip is constructed from a polydimethylsiloxane (PDMS) mold. It includes two hydrophilic microchannels as shown in FIG. 2A, with other views shown in FIG. 2C and FIG. 2D. Each microchannel is connected to and originates from the same inlet through which a sample (e.g., blood) is dispensed, so as to provide feasibility of detecting different disease antigens from the same sample at the same time. The microchannels depicted in FIG. 1 have a width of 200 µm, though widths ranging between 50 and 1000 µm are also contemplated.

Continuing to refer to the biochip of FIG. 2A, each microchannel may include three gold nano IDEs so that the biochip includes six in total. Each IDE is coated with a particular and unique antibody. The biochip also includes contact pads which serve to connect each IDE with probes of an electrochemical analyzer(s) to record and analyze readings taken from each IDE. Both IDEs and contact pads are fabricated on a silicon substrate. The IDEs are connected to individual contact pads so that the signal from each IDE can be separately monitored. In this manner, a specific antibody can be immobilized at a specific IDE so that the concentration of the corresponding antigens can be detected by the antigen-antibody complex formed at that IDE. Detection of a concentration of separate individual antigens in the sample via the separate IDEs can enhance the detection specificity. Thus, an advantage of this biochip is that several types of antigens can be detected simultaneously through a single sample drop. For example, the biochip depicted in FIG. 2A can sense the presence of up to six different antigens such as cancer, pneumonia, lung cancer and pancreatic cancer, to name a few. This in turn results in an improved specificity of results, particularly when compared with a biochip having a single electrode and a single pair of contact pads. Another advantage of the biochip is that through its simplicity and portable size, it can be used to perform diagnostic testing in convenient locations, such as in the home or office.

The biochip can be varied in many ways. For example, three, four or more microchannels extending from the inlet can be included on the biochip. Each microchannel can include two, three, four or more IDEs, and each microchannel can have a different number of IDEs than another microchannel. In another example, multiple electrodes spaced apart from one another can be connected to a single pair of contact pads. This can be done for one or more pairs of contact pads. The incorporation of additional electrodes for a particular circuit provides a structure that senses the biological reactions at multiple locations of a microchannel. It also multiplies the effect of the sensing mechanism to enhance the detection sensitivity. In this manner, the biochip structure depicted in FIG. 2A can be combined with features that enhance sensitivity to create a biochip with both improved specificity and sensitivity.

In yet another example, the microchannel of the biochip can be a spiral configuration. Sample flow in the spiral configuration benefits from a centrifugal effect due to the microchannel shape. Other microchannel shapes other than those already described are also contemplated.

In another example, the mold for the biochip can be a material other than PDMS, including many biocompatible polymers. It is contemplated as within the scope of the invention that materials for the mold are not limited to those that are receptive to oxygen plasma treatment, and when other materials are used, other treatments effective to make the mold surface hydrophilic are also contemplated. Some specific examples of other mold materials include glass and ceramics.

In yet another example, conductors other than gold can be used for the IDEs. Generally speaking, any material with good conductivity can be used, such as silver and platinum. Conductors that are the most chemically stable can be chosen when multiple options are available.

In another aspect, described in greater detail as part of the experiment below, the biochip PDMS mold and accompanying microchannels can be manufactured using 3D printing. An advantage of 3D printing is that it increases the possibilities for microchannel design and thus provides increased flexibility. It is also contemplated that other biocompatible polymers capable of manufacture using 3D printing can be used.

Figure 2D:
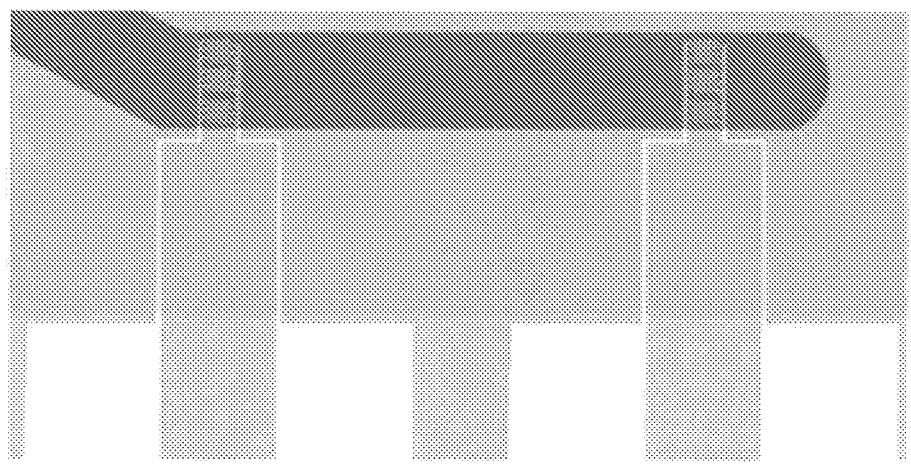
FIG. 2D illustrates a partial close up view of the biochip of FIG. 1A.

In yet another aspect, the invention relates to a method of performing a disease diagnostic test. In one embodiment, a sample is deposited into the inlet of the biochip. Once the sample passes the inlet, it splits into each of the microchannels, which both originate at the inlet. The sample then advances simultaneously in each of the microchannels through a capillary effect described in greater detail below. When the sample in each microchannel reaches an IDE (or a second IDE, as shown in FIG. 2C and FIG. 2D), a biomolecular reaction may occur if there is an antigen or other biomolecule that causes a biomolecular reaction in response to its contact with the antigen or other biomolecule on the IDE. If a biomolecular reaction takes place, electrical measurements, such as capacitance, taken by the IDE before and after the sample reaches the IDE, will show a change in value. This in turn is signaled to a user of the biochip via contact pads connected to the IDE and from there to probes of an electrochemical analyzer, where data may be produced for a user to view. Further explanation on how the biochip uses electrical properties to sense biochemical reactions at the IDEs is provided below.

In the biochip of FIGS. 2A-2D, the above process takes place at each IDE for each microchannel. In the configuration shown, specificity of diagnostic results is greatly improved over existing approaches because each of six IDEs (A+/A−, B+/B−, C+/C−, D+/D−, E+/E− and F+/F−) can include a unique antibody. As mentioned above, the antibody can be any desired to be tested and is not limited. In this manner, a single sample drop can be analyzed for the presence of up to six different pathogens. Once the sample passes the final IDE in each microchannel, i.e., C+/C− and D+/D−, the sample advances to the outlet and exits the biochip.

In a variant, the method can be employed using any other biochip contemplated herein. Non limiting examples of such variations include performance of the method with biochips having different microchannel configurations, a different number of microchannels, different materials and/or different configurations and quantities of IDEs on the biochip.

Figure 3:
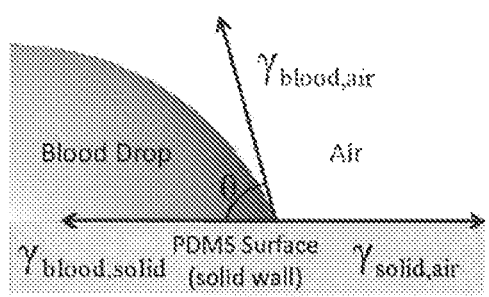
FIG. 3 is a schematic of a blood drop on a poly (dimethylsiloxane)(PDMS) surface.

The contact angle of a liquid drop on a solid surface is defined by the mechanical equilibrium of the drop under the action of the interfacial tensions. The three interfacial tensions observed when a blood drop is placed on a solid, such as a PDMS surface, are $\gamma_{blood,air}$, $\gamma_{blood,solid}$ and $\gamma_{solid,air}$, where $\gamma_{blood,air}$ is the interfacial tension between blood and air, $\gamma_{blood,solid}$ is the interfacial tension between blood and PDMS substrate and $\gamma_{solid,air}$ is the interfacial tension between the PDMS substrate and air as shown in FIG. 3.

As per Young's law, $\gamma_{solid,air} = \gamma_{blood,solid} + \gamma_{blood,air} \cos\theta$ (1)

From the above Equation (1), the contact angle $\theta$ can be calculated per the derived Equation (2), $$\theta = \cos^{-1}\left(\frac{\gamma_{solid,air} - \gamma_{blood,solid}}{\gamma_{blood,air}}\right) \quad (2)$$

Figure 4:
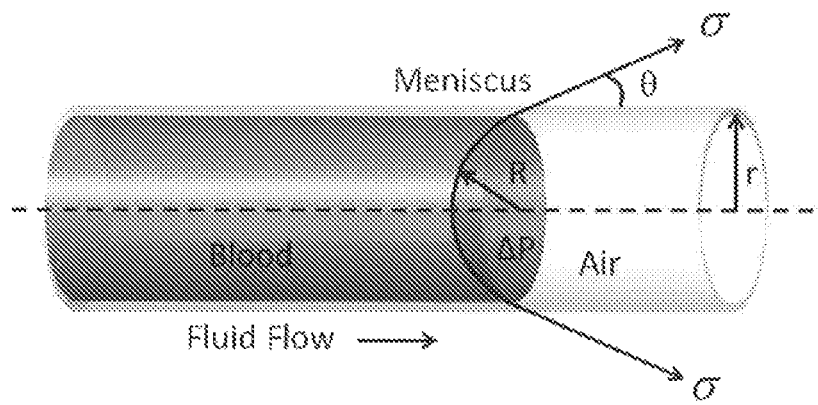
FIG. 4 illustrates a schematic of bio fluid flowing in capillary channel due to surface tension.

Surface tension causes a capillary pressure difference across the interface between two fluids (liquid and air). Seen in FIG. 4 is a microchannel of circular cross section with radius "r" filled with two immiscible fluids with surface tension σ. The meniscus can be approximated as a portion of a sphere with radius "R." The pressure difference across the meniscus is defined by Equation (3):

$$\Delta P = -\frac{2\sigma}{R} \quad (3)$$

The radius "R" of the meniscus will depend only on the contact angle θ and the radius of the channel "R" seen in Equation (4):

$$\Delta P = -\frac{2\sigma \cos\theta}{R}. \quad (4)$$

Altering the contact angle of the fluid with specially treated surfaces will help in controlling the surface tension driven flow. The surface tension gradient primarily depends on temperature gradient, concentration gradient, electric field and the contact angle variation. In order to preserve the natural properties of the sample of bodily fluid, in this example blood, in a diagnosis process, the concentration of the blood or the temperature of the blood should not be altered. Altering the contact angle is a way for controlling the surface tension effect on the capillary flow of blood in the microchannel.

Figure 5A:
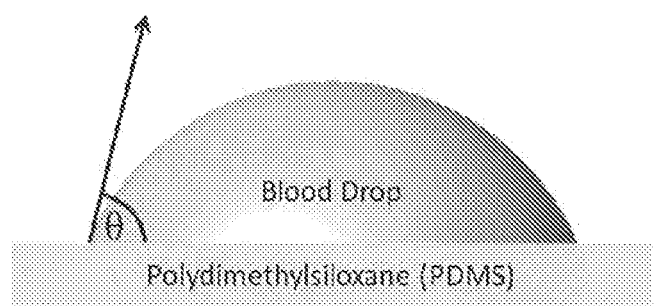
FIG. 5A illustrates a schematic representing relationship between contact angle and hydrophobicity of PDMS surface.

Depending on the embodiment, one or more microchannels may be fabricated with a 3D printer using a material such as PDMS (polydimethylsiloxane). PDMS by nature is a hydrophobic surface that is not conducent to use with fluid analysis (whose contact angle is greater than 90 degrees) which resists the wettability of fluid on the surface. For the liquid to flow naturally, a hydrophilic surface (whose contact angle is less than 90 degrees) is required as shown in FIG. 5A.

The hydrophobic nature of the PDMS can be altered to a hydrophilic nature by performing various surface treatments like for example, such techniques that include, but are not limited to, active group attachments, Oxygen plasma treatment or other plasma treatment, chemical coating, thermal aging, and any combination thereof. In the example given herein, oxygen plasma treatment was used to convert hydrophobic nature of PDMS to hydrophilic nature. The hydrophilicity attained by surface treatment is sustained depending on factors like the temperature and humidity of the environment in which the PDMS mold is preserved.

Figure 5B:
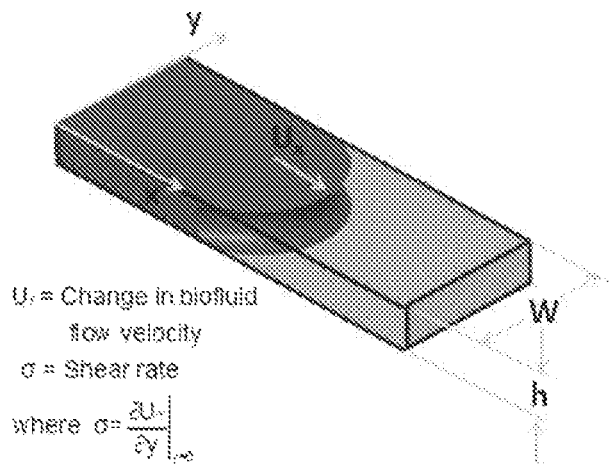
FIG. 5B is a schematic of a microchannel with a shear rate measurement.
Figure 5C:
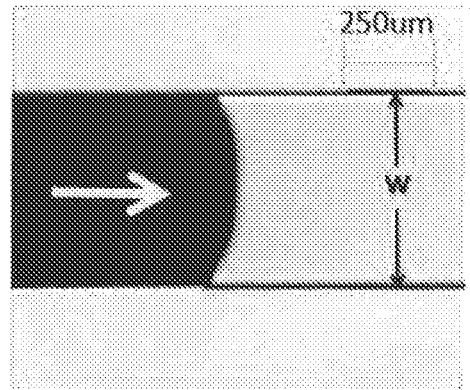
FIG. 5C is an image of the microchannel during flow of a biofluid sample.

Microfluidic flow of biofluid was investigated. In one embodiment, the microchannel with a width of 'w' (515 um) and of depth 'h' (107 um) was employed to generate the microfluidic flow on the sensing platform as shown in FIGS. 7D, 7E and 7F. The biofluid flow in the microchannel generates a shear on the sensing surface. The shear rate is defined by the change in the biofluid flow velocity ($U_x$) with respect to the microchannel height at the microchannel surface (y=0) and it is calculated by applying the boundary conditions of Poiseuille flow as shown below in the following equation:

$$\sigma = \frac{\partial U_x}{\partial y}\bigg|_{y=0} \approx \frac{6Q}{wh^2}$$

Where Q is the flow rate of the biofluid which is measured as 0.25 uL/sec (FIG. 5B). Thus the shear rate ($\sigma$) is calculated as 294.11 sec$^{-1}$. The shear rate influence on the stability of the immobilized disease antigens antibodies on the sensing surface and the corresponding effect on sensitivity of the antigen-antibody interaction. Typically found was as the shear rate increases the sensitivity of the antigen-antibody interaction decreases. This effect was determined due to the reduced stabilization of the antibodies due to the shear stress. FIG. 5C is the microscopic image during the biofluid flow in microchannel.

In one embodiment, the oxygen plasma treatment of the PDMS introduces polar functional groups such as the Silanol groups (SiOH) on the surface of the PDMS. The silanol groups are responsible for converting the PDMS property from hydrophobic to hydrophilic as shown in FIG. 6. The oxygen plasma treatment also helps in increasing the adhesion property of the PDMS, so that it can be easily bonded with other substrates or another PDMS slab. However, the surface treatment due to Oxygen plasma treatment is not permanent. PDMS regains its hydrophobicity after a certain period (for example 6 hours). Thus, by treating the PDMS microchannel with plasma treatment, the contact angle can be altered and therefore the capillary effect caused by the surface tension can be controlled. By controlling the capillary effect, the flow in microchannel primarily dependent on the capillary effect can also be controlled.

The sensing mechanism is implemented, depending on the embodiment, using a non-optical methodology like an electrical methodology. This methodology will drastically reduce the setup cost and enhance the accuracy of the results. In the present POC micro biochip, an electrical methodology (measuring change in capacitance for example) is implemented for the sensing antigen-antibody interaction as shown in FIGS. 7A, 7B, and 7C. FIG. 7A illustrates one embodiment of a POC micro biochip functionality during a body fluid sample flow in microchannels when nano electrodes, in this example connected in series-, is utilized. Depending on the embodiment the electrodes may be connected in parallel. Again, the body fluid may be blood or other patient body fluid such as but not limited to salvia, urine, tears, blood, secretions, and the like. The electrical biosensor detects the biomolecular reactions with the changes in electrical properties like voltage, current, impedance, capacitance, resistance, and any combination thereof. The approach of measuring the capacitance has advantages like high sensitivity, even for small changes (femto scale), freedom of sensor size variation and low power consumption requirement. FIG. 7B illustrates the body sample after interaction with antibodies and FIG. 7 C shows the body sample before interaction with antibodies.

FIGS. 7 D, 7E, and 7F illustrates microfluidic flow of disease antigens that was employed by attaching the microchannel on the sensing surface and passing the biofluid or sample through the microchannel as shown in FIG. 7D. The PDMS microchannel was fabricated primarily in two steps (1) fabrication of Si-mold with protruded microchannel (2) The PDMS microchannel from the Si-mold.

First step: The Si-mold with microchannel was fabricated at the Center for Functional Nano materials at Brookhaven National Laboratory, Upton, N.Y. A silicon wafer of 4 inch diameter and 1 mm thickness was used for Si-mold to fabricate the microchannels on it. Si-wafer was cleaned with acetone, Isopropanol alcohol and DI water. The wafer was dehydrated at 115° C. for about a minute using a hot plate and later allowed it to reach the room temperature. A positive photoresist (SPRTM 955) was deposited on top of the wafer. The Si wafer, which was coated with photoresist, was placed on a spin coater and rotated at 1200 rpm for one minute to achieve the required thickness of photoresist on the wafer. Photoresist coated Si-wafer was placed on the UV fight exposure tool (Karl Suss MABA6) and exposed to UV rays for 14 seconds. Due to UV exposure, the area which was not covered by the mask became soft. The wafer needs to be treated with CD-26 chemical and DI water to remove the photoresist remaining on the wafer on the UV exposed area. A Deep Reactive ion Etching (DRIE), also called the Bosch process was used to etch a depth of 107 um, Areas that are not covered by the photoresist are etched from the Si wafer. Thus the microchannels of height 107 um were formed on the Si wafer.

Second step: The Si-mold (S-wafer with microchannel) was used to fabricate the PDMS with microchannel. The PDMS base was mixed with the curing agent at 10:1 ratio and was kept in the vacuum chamber to degas the air bubbles. The PDMS mixture was poured on the Si-mold and degassed again under vacuum, to remove any air bubbles that were formed. Then the PDMS mixture with Si-mold was baked at 125° C. for 20 minutes. Then the baked PDMS mold was removed from the Si-mold gently. This forms the cavity of microchannel on the PDMS layer. The inlet and outlet holes are made to the microchannel so that the fluid sample can flow through it. The PDMS microchannel was treated with oxygen plasma for 100 sec with 'plasma cleaner—PDC 32G' in order to covert its hydrophobic nature to hydrophilic nature and also to attach the Si-wafer to the PDMS mold. The PDMS microchannel was thus closed with the Si-wafer with interdigitated electrodes, so that the microchannel has 3 sides with PDMS surface and one side with Si-wafer surfaces with sensing platform as shown in FIGS. 7D, 7E, and 7F.

When gold is used as interdigitated electrodes (IDE), which are in nanoscale, the IDE identifies the nano scale variations in electrical measurements like capacitance or impedance. It has been proven that the sensitivity of nanoscale is much higher and better as compared to conventional micron electrodes as the electric field generated by the nano scaled electrodes ranges from 100 nm-200 nm which fulfills the region of interest, since antigens and antibodies lies in this range. The space confinement between the interdigitated electrodes in nanoscale helps in minimizing the noises from the detection signal. The insulation on top of the gold interdigitated electrodes is critical, in order to avoid the chances of short circuit and minimize the noise.

Self-assembled monolayer (SAM) primarily helps to provide proper insulation. SAM layer forms significantly better adhesion on top of gold, for example, when compared to any other oxides or semiconductors. CA 125, a prominent cancer antibody, is used in the below experimental example. Again other biomarkers like kallikreins (KLK6 & KLK 7) which are highly active at the earlier stages of the diseases like ovarian cancer as well as other biomarkers may be utilized with the present invention in being immobilized on the electrodes. The capacitance between the two electrodes is given by Equation (5) below, $$C_{Geometry} = \varepsilon_r \cdot \varepsilon_0 \frac{A}{d} \quad (5)$$

Where $\varepsilon_r$ is the relative permittivity of the material between the two electrodes and $\varepsilon_0$ is the vacuum permittivity, A is the electrode surface area, and d is the distance between two electrodes. It can be inferred from this equation (5), that a significant change in the capacitance can be caused in three ways: (i) by altering the distance d between the two electrodes, (ii) by altering the overlapping area A between the two electrodes and (iii) by a change in the dielectric permittivity between the electrodes. For the simplified case assuming the interdigitated electrodes are sufficiently thick, the resistance in the solution is given by, Equation (6):

$$R_{Solution} = \frac{1}{nl}\frac{1}{k}\frac{2\left(\sin\frac{\pi W_{sp}}{2L}\right)}{\left(\cos\frac{\pi W_{sp}}{2L}\right)} \quad (6)$$

Where n is the number of fingers and l is the length of fingers of the interdigitated electrodes, k is the conductivity of the bio fluid sample, $W_{SP}$ is the spacing between the electrodes and L is the width of the electrode and spacing between electrodes.

The antigen (Ag)—antibody (Ab) interactions are highly selective. The change in the net molecular size due to antigen/antibody complex (Ag/Ab) formation creates a disturbance in the distribution of charges, by creating a dipole moment at the dielectric interface. The hydrocarbon chains present in the proteins are polar in nature. The net charge variation due to the interaction of the hydrocarbons of antibodies and antigens, create a process of local polarization that directly influences the dielectric permittivity of the complex on the electrode surface. The dipole-dipole interaction stimulates the polarization on the electrode surface. With this phenomenon, the dielectric of each antigen/antibody complex over the range of frequencies has unique characteristic that helps to identify the complex formation. As a result, the measured capacitance of the sensor varies with the relative changes in dielectric properties on sensor surface.

Figure 8A:
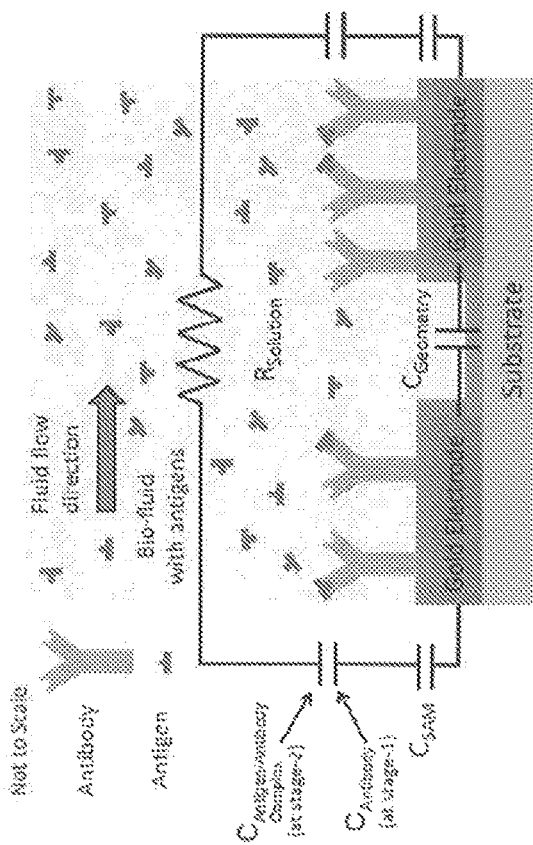
FIGS. 8A and 8B illustrate schematic representations of capacitance sensor circuit design in a biochip.
Figure 8B:
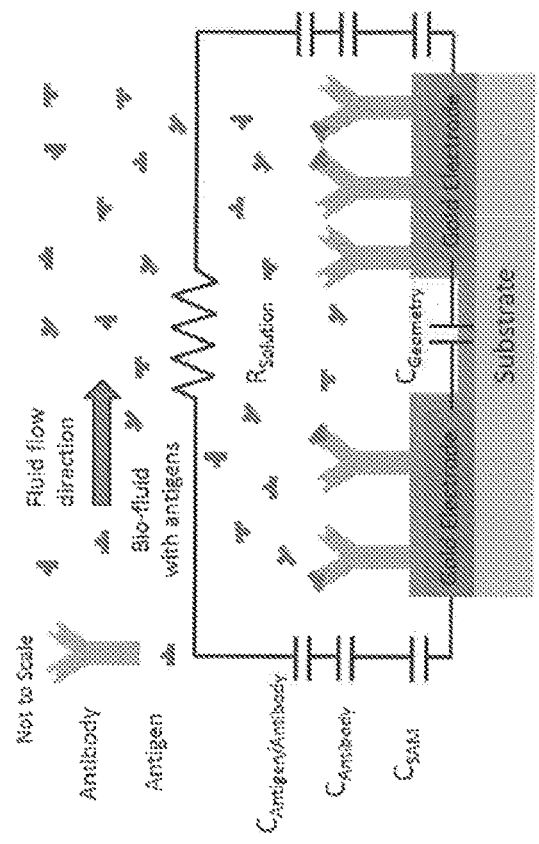
Figure 9:
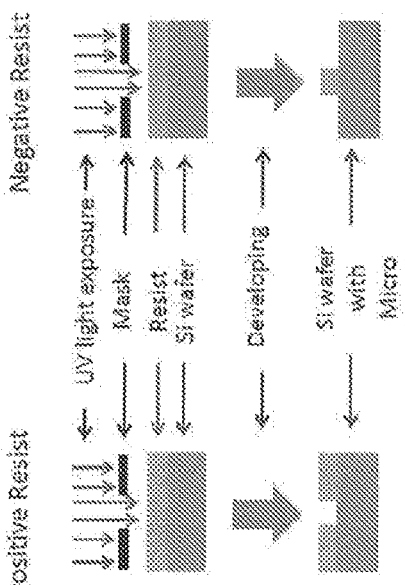
FIG. 9 illustrates measurement of capacitance variation during antigen indentation.

The capacitances are measured at two stages in the experiment. In the first stage (stage-1), the capacitance is measured before the antigen and antibody complex formation ($C_{Baseline}$) as shown in Equation (7), where $C_{Geometry}$, $C_{SAM}$ and $C_{Antibody}$ are the capacitance due to bare gold nano interdigitated electrodes, the SAM layer and the antibodies. When the blood flows through the microchannel, the disease specific antigens in the bio fluid interact with the antibodies that are immobilized on the surface of electrodes, and form the antigen-antibody complex. In the second stage (stage-2), capacitance is measured after the antigen/antibody complex formation $$C_{Baseline} = C_{Geometry} + \left[\frac{1}{C_{SAM}} + \frac{1}{C_{Antibody}}\right]^{-1} \quad (7)$$

$$C_{\substack{TOTAL \\ Antigen/Antibody}} = C_{Geometry} + \left[\frac{1}{C_{SAM}} + \frac{1}{C_{\substack{Antigen/Antibody \\ Complex}}}\right]^{-1} \quad (8)$$

$$\Delta C = C_{\substack{TOTAL \\ Antigen/Antibody}} - C_{Baseline} \quad (9)$$

$$\left(C_{\substack{TOTAL \\ Antigen/Antibody}}\right)$$

as in Equation 8, where $$\left(C_{\substack{Antigen/Antibody \\ Complex}}\right)$$

is the capacitance due to Antigen/Antibody complex formed. The difference in capacitance ($\Delta C$) between stage-2 and stage-1, provides the information of capacitance change caused due to antigens in the bio fluid sample, as in Equation (9). The resistance of solution ($R_{Solution}$) as in Equation (6), is considered. This change in capacitance provides information about existing disease antigen in the bio fluid as shown in FIGS. 8A-8B and FIG. 9.

Example 1

The following experimental techniques and instruments were used to test the use of inventive device and method. While the following example illustrates the invention's use with PDMS microchannel fabrication using a Si wafer and diagnostic testing of a single blood sample for reaction with CA125, the invention is not limited to using PDMS or a Si wafer or testing blood or testing blood for CA125.

The primary steps involved in the fabrication of hydrophilic PDMS microchannel are: Fabrication of Silicon Wafer with microchannels, PDMS mold fabrication using Si wafer, Surface treatment of PDMS (hydrophobic to hydrophilic).

The Silicon wafers with microchannels are fabricated at the Center for Functional Nano materials at Brookhaven National Laboratory, Upton, N.Y. A silicon wafer of 4 inch diameter and 1 mm thickness is used to fabricate the microchannels on it. An ample Si-wafer thickness (1 mm) is chosen, since the channel structures are etched from Si wafer which are 100 μm to 200 μm height. Depending on the embodiment the height may range from 100 μm-1000 μm and preferably be about 200 μm.

Figure 10:
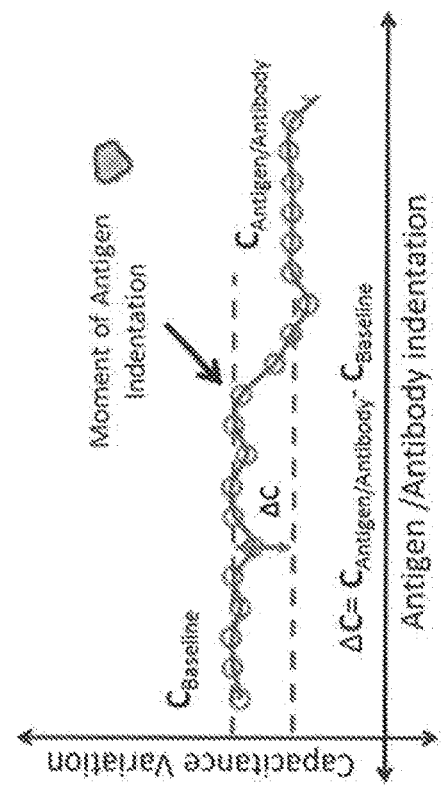
FIG. 10 illustrates schematic representation of photolithography process for both positive and negative resist on Si wafer.

A Silicon Wafer of 4-inch diameter was cleaned with acetone, Isopropanol alcohol and deionized (DI) water. The wafer was dehydrated at 115° C. for about a minute using a hot plate and kept on a cold plate to attain room temperature. A negative photoresist (SPRTM 955) was deposited on top of the wafer. The negative photoresist was used to remove the material other than the channel area. The Si wafer, which was coated with photoresist was placed on a spin coater using a specific size chuck and the spin coater was rotated at 1200 rpm for one minute, which removes the excess photoresist, leaving a thin layer of (micro meters) of SPRTM 955 on the wafer. Coated Si-wafer was placed on the UV light exposure tool (Karl Suss MABA6) with exposure time as 14 seconds. Due to UV exposure, the area which was not covered by mask became soft. The wafer needs to be treated with CD-26 chemical and DI water to remove the photoresist remaining on the wafer on the UV exposed area. Wafer is then dried with a nitrogen gun to remove any water content as shown in FIG. 10.

A Deep Reactive Ion Etching (DRIE), also called the Bosch process was performed to etch more depth (107 um). Areas not covered by the photoresist were etched from the Si wafer, so that the channels were formed. The height of the channels attained is 107 μm as shown in FIG. 11A and FIG. 11B.

PDMS Base was blended with a curing agent in definite *proportion* (1:10). Thorough mixing (about 10 minutes of whisking) was needed to make sure that the curing agent was uniformly distributed. This ensured that the final PDMS mold was uniformly cross linked between base and curing agent. Degassing was performed multiple times so that all the air bubbles trapped in the PDMS mixture were removed. Curing of the PDMS primarily depends on temperature and time.

The curing temperature is indirectly proportional to the time. The PDMS was cured at 100° C. for 35 minutes. When PDMS was suitably cured, application of a steady pressure should help peel off the PDMS from Si wafer mold, as shown in FIG. 13.

Though PDMS is a soft material, punching a hole at the inlet and outlet of the microchannel was a critical process due to the micro dimensions. The micro hole punching machine (Central Machinery, 5-Speed bench drill press) was used to make holes in the PDMS mold. These holes act as inlet and outlet for the microchannels. The PDMS molds were treated with oxygen plasma and placed against Si wafer with electrodes and immobilized antibodies, to form the closed microchannels. The PDMS mold with serpentine microchannel is shown with the inlet and outlet of the fluid flow in FIG. 12A and FIG. 12B.

Figure 14:
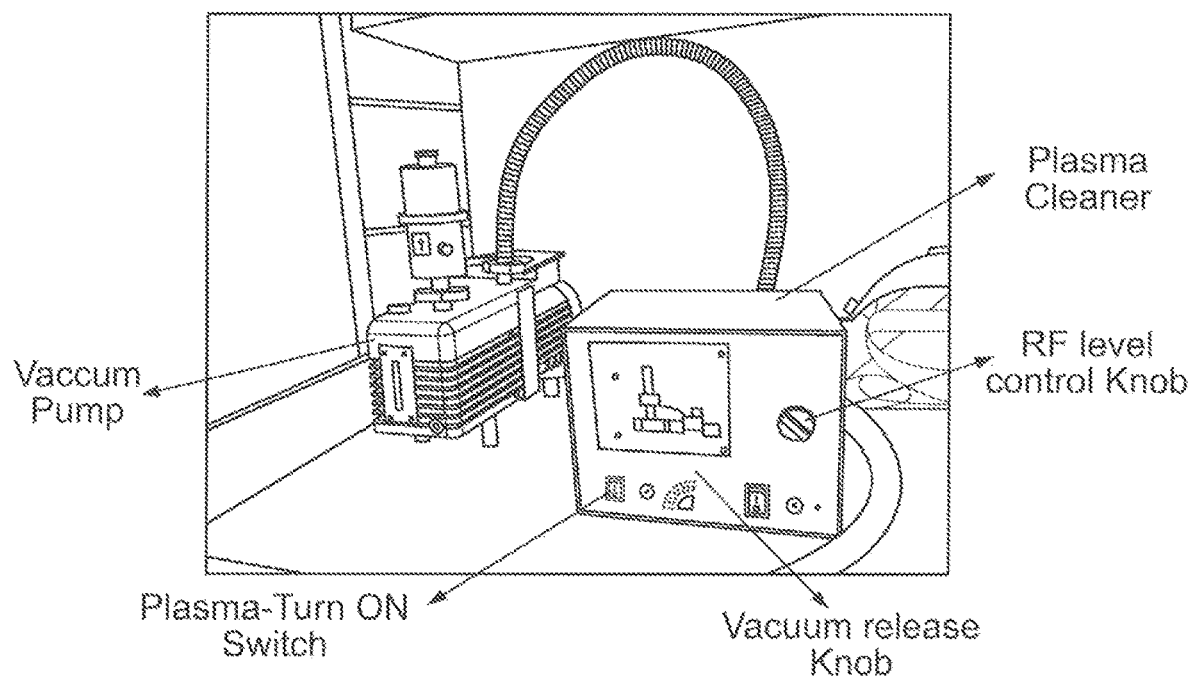
FIG. 14 illustrates oxygen plasma treatment equipment.
Figure 15:
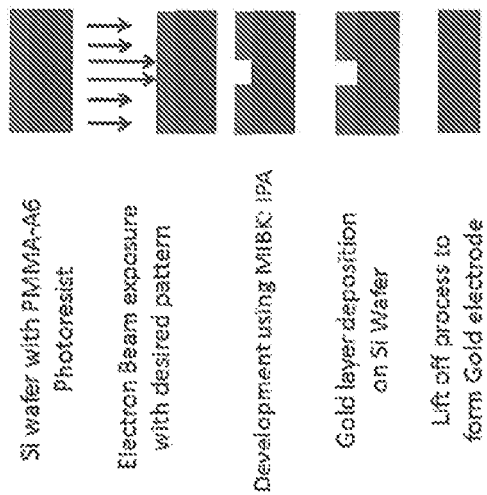
FIG. 15 illustrates a schematic of a gold nano interdigitated electrode fabrication process.

PDMS surface is highly inert and hydrophobic in nature. In order to convert the PDMS to hydrophilic in nature, the PDMS was exposed to oxygen plasma for various durations. In this experimental example, the hydrophilicity of PDMS was measured with respect to variation in duration of the plasma treatment. All plasma treatments were conducted on the 'Plasma Cleaner PDC-32G' with an oxygen flow rate of 20 sccm and 100 bar pressure. A radio frequency (RF power supply of 150 W) of 13.56 MHz was used for plasma excitation. FIG. 14 shows the plasma treatment equipment used for this experimental example.

The primary steps involved in the fabrication of gold interdigitated electrodes were: Fabrication of gold nano interdigitated electrodes and CA-125 Antibody immobilization on Electrodes.

A Silicon (Si) wafer was cut as per the dimensions desired and cleaned with isopropanol before starting the electrode fabrication. The Silicon wafer was then spin coated with positive tone photoresist. The photoresist used was PMMA-A6. The desired thickness of electrodes was 100 nm. Although depending on the implantation other thicknesses may be utilized. Ideally, the height of the PMMA deposits should be more than 3 times the height of the electrodes. The soft baking of the Silicon wafer was performed on a hot plate at around 180° C. for 120 seconds. The coated Silicon wafer then undergoes Electron beam Lithography procedure as per the CAD model provided for the EBL machine. The desired pattern (Interdigitated) was formed on top of the coated Silicon wafer. The patterned Si wafer was then developed with MIBK:IPA for 60 s and washed with IPA for another 60 s and then dried with Nitrogen gas. Once developed, the Silicon wafer was placed in a Physical vapor deposition machine for deposition of metal on the wafer. A layer of Titanium (approx. 10 nm) was deposited on the patterned grooves of the chip. This was done to improve the adhesion of gold on Silicon. Gold was deposited over the wafer by high vacuum evaporator (Kurt J Lesker PVD-75 Evaporator). A layer of approximately 90 nm of Gold was deposited on top of the Si wafer. The lift-off process was performed by removing the positive tone photoresist by cleaning the wafer in Acetone Ultrasonic bath for 3 minutes and then thoroughly rinsed with Isopropenol in order to prevent redeposition. The fabricated wafer with gold deposition was then rinsed with distilled water and dried with Nitrogen gas. The electrodes were fabricated by following the fabrication steps as shown in FIG. 15, FIG. 16A, FIG. 16B and FIG. 17A, FIG. 17B, FIG. 17C.

Figure 16B:
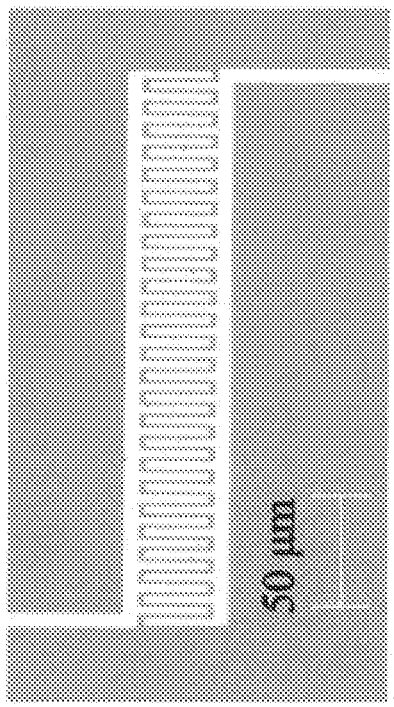
FIG. 16B is another microscopic image of a gold interdigitated electrodes on a Si wafer.
Figure 16A:
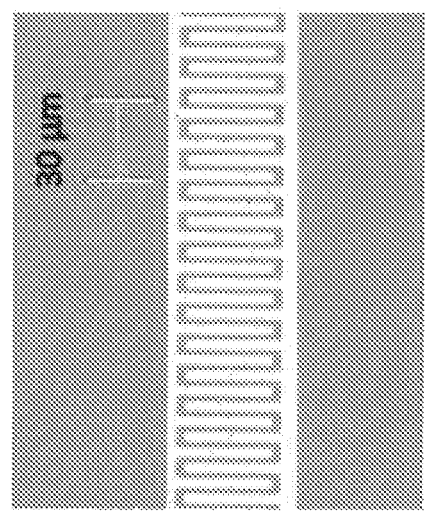
FIG. 16A illustrates a microscopic image of gold interdigitated electrodes fabricated on the Si wafer.
Figure 19:
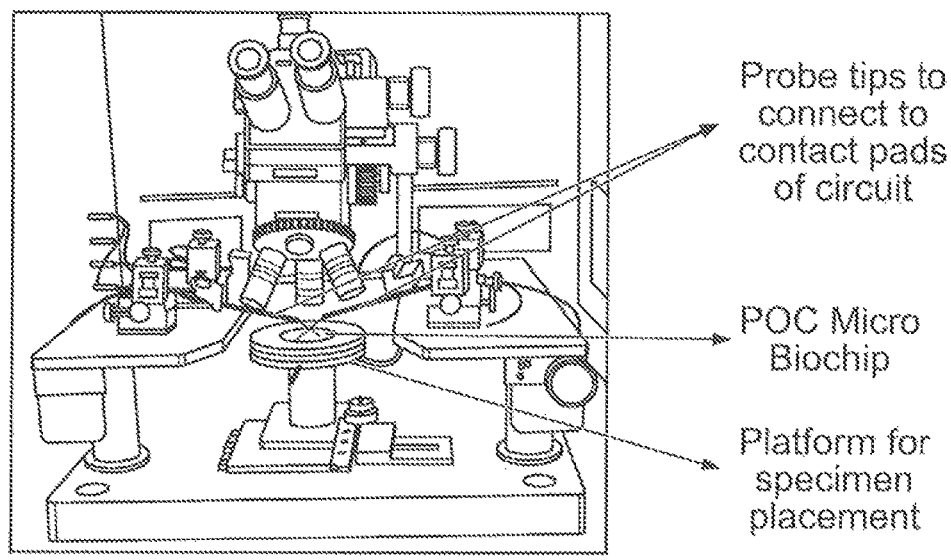
FIG. 19 illustrates an electrical probe station to detect capacitance change due to Antigen/Antibody complex formation.

FIG. 16A, FIG. 16B, and FIG. 17A show the microscopic images of the interdigitated electrodes fabricated on the Si wafer for the experimental example. The gold nano electrodes were insulated using the SAM (Self-assembled monolayer) and then coated with antibodies. The electrodes were immersed in a 50 mM Thiourea solution for 12 hours to form the SAM layer. The surface of the sensor was then rinsed with ethanol and Millipore deionized water and dried using Nitrogen gas. For enhanced antibody binding, Glutaraldehyde was utilized to promote surface activation on the SAM layer. The CA-125 antibodies were aliquoted to a concentration of 10 ng/ml, and placed on top of the surface activated SAM layer at 4° C. for 12 hours to immobilize the antibodies. FIG. 19 illustrates an electrical probe station to detect the change in electrical properties of the nano circuit of the POC biochip. In this example the change in capacitance is monitored. Again, the scope of the invention is not so limited to monitoring change in capacitance and can be utilized to monitor any change in electrical property or combination of electrical properties.

Surface characterization of different layers on sensing platform was examined. The modifications of the silicon substrate with each layer of sensing platform were validated using the AFM measurements. AFM images were taken to confirm the fabrication of interdigitated electrodes, SAM layer on the interdigitated electrodes and antibody immobilization on the electrodes. In FIG. 17A, the relatively smooth surface of the bare electrodes when compared to the surface with SAM layer on the electrodes was observed. When the antibodies were immobilized on the electrodes with SAM layer a more rough surface morphology was observed. Quantitative increase in the roughness of the electrode surface at individual layers is observed. AFM images of the surface of the interdigitated electrodes with Bare electrodes indicated the roughness. In FIG. 17B shown is an AFM image of the SAM layer and in FIG. 17C immobilized antibodies.

The increase in the net height of the electrodes and surface roughness confirms the formation of the SAM layer and antibody immobilization on the electrodes. The capacitive measurements additional to AFM image confirm the SAM layer insulation and the antibodies immobilization on the electrodes.

In one example, a 10 mM of 1-dodecanthiol in ethanolic solution was added on top of the electrodes to block the unwanted sites or the bare spots on electrode surface. The PDMS microchannel was aligned with the nano patterned interdigitated circuit to have the blood sample flow on the cancer antibodies that are attached to the surface of the electrodes as shown in FIG. 1A and FIG. 2A.

FIG. 18A illustrates a chemotic representation of CA-125 antibody immobilization on nano gold interdigitated electrodes.

Figure 18B:
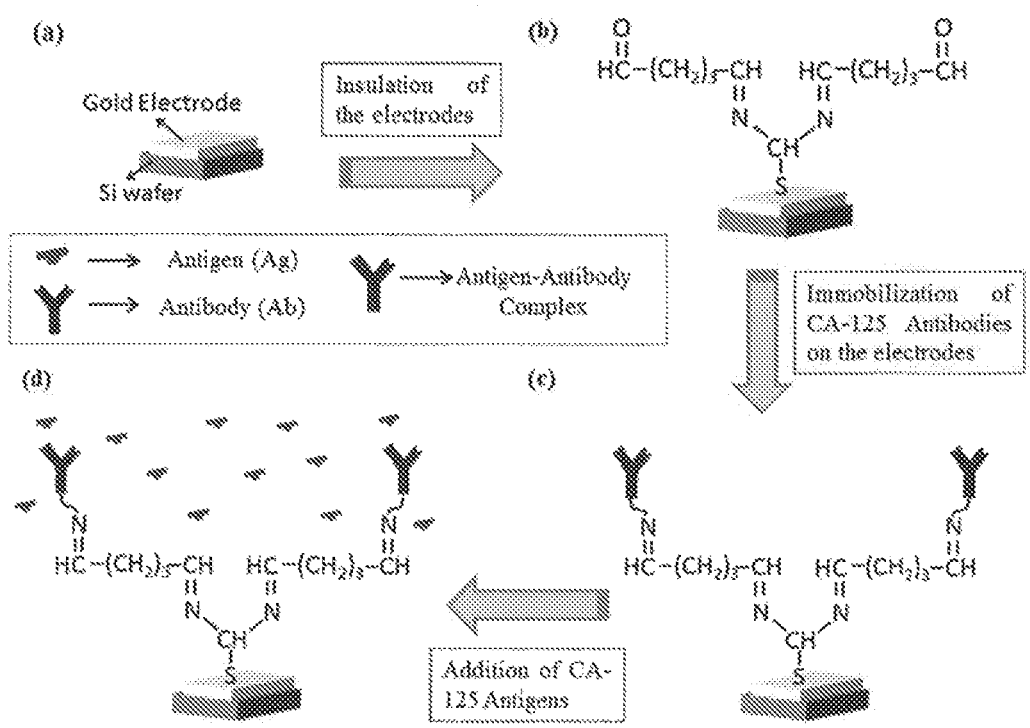
FIG. 18B illustrates a schematic of steps implemented to setup an experimental trial of biosensing (a) gold interdigitated electrodes on a Si wafer, (b) insulation of electrodes using surface activated SAM layer, (c) antibodies immobilization and (d) antigens binding with the immobilized antibodies.

FIG. 18B illustrates a schematic of steps implemented to setup an experimental trial of biosensing (a) gold interdigitated electrodes on a Si wafer, (b) insulation of electrodes using surface activated SAM layer, (c) antibodies immobilization and (d) antigens binding with the immobilized antibodies. The biofluid sample in one example was 55 ug/ml of disease antigens concentration in PBS solution at pH 7.4. The biofluid sample was passed on the immobilized antibodies on the electrodes, to form antigen-antibody interaction as shown in FIG. 18B.

Further depending on the embodiment, gold interdigitated electrodes on Si-wafer were washed for 3 times with ethanol and de-ionized water and dried with the Nitrogen gas. Then the electrodes were immersed in a 50 mM Thiourea solution ($CH_4N_2S$) and incubated for 12 hours to form the SAM layer Self-assembled Monolayer (SAM layer). To remove the excessive Thiourea solution, the surface of the electrode was rinsed with ethanol and Millipore deionized water and then dried using Nitrogen gas. The electrical insulation of the SAM layer was confirmed by evaluating the short circuit/current leakage using the 2 point probe station. Glutaraldehyde ($C_5H_8O_2$) was used to promote the surface activation on the SAM layer, for enhanced antibody binding to the electrodes shown in FIG. 18A and FIG. 18B.

Immobilization of disease antigens antibodies on the electrodes was accomplished in one example as follows. The disease antibodies were immobilized on the gold interdigitated electrodes by incubating the electrodes with 0.5 ul of 7 mg/ml antibodies in Phosphate-buffered saline (PBS) solution for 2 hours at 4° C. A 10 mM of 1-dodecanthiol in ethanolic solution was added on top of the SAM coated electrodes to block the unwanted sites or the bare spots on electrode surface for 1 hour. Thus the antibodies were immobilized on the gold interdigitated electrodes on Si-wafer as shown in FIG. 18A and FIG. 18B. The consistency of the antibodies immobilization on the electrodes for all the experiments and at all the iterations was verified using the surface characterization and electrical measurements in order to maintain uniform sensing conditions.

A Signatone electrical probe station was used to determine the capacitance variation of the antigen indentation with the antibody as shown in FIG. 19. The change in capacitance is measured with the logarithmic value of the concentration of the antigen. The change in variation indicates the existence of the cancer antigen in the blood sample, since the cancer specific antibodies (CA-125) are coated on the sensing platform of the biochip.

Figure 20:
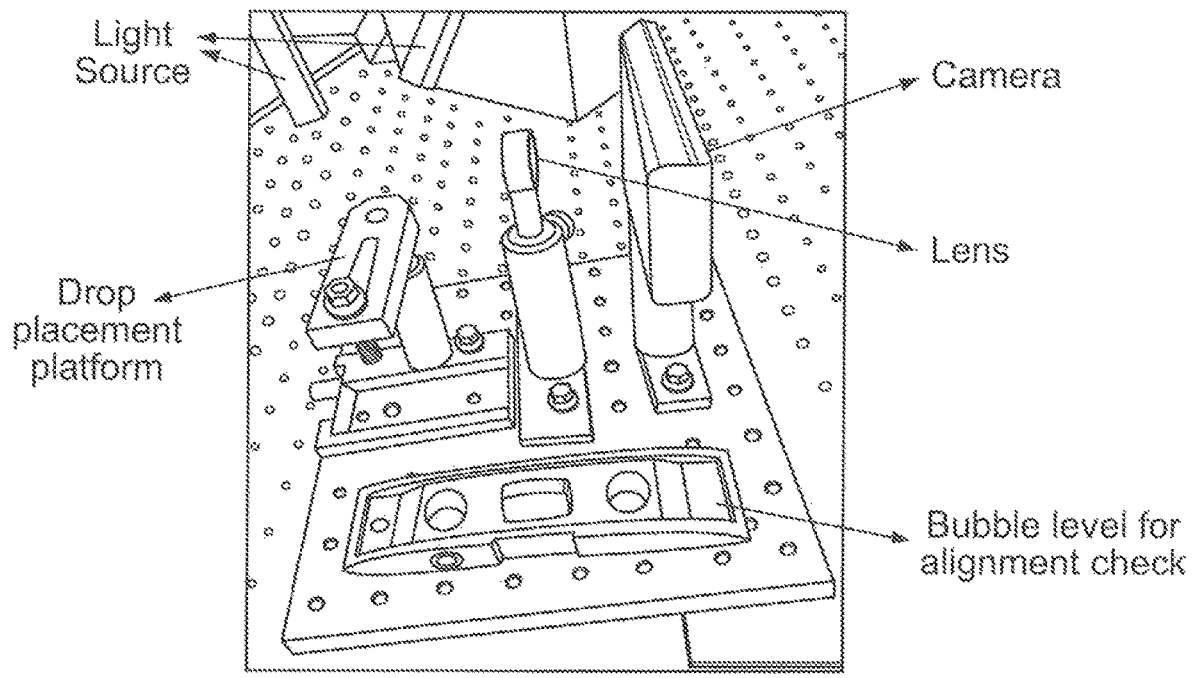
FIG. 20 illustrates a setup for imaging blood drop to measure the contact angle.

The Results of the experimental example were as follows. The contact angle measurements were done using the custom made contact angle measurement system known in the art. This setup consists of optical lens with a 50 mm diameter (Thorlabs, BK7 A-coated plano-convex lens, 25.4 mm diameter) and a Sony cyber shot digital camera (8-mega pixels resolution). The contact angle measurement setup is shown in FIG. 20. The static contact angle measurements were made based on sessile drop technique.

Figure 21:
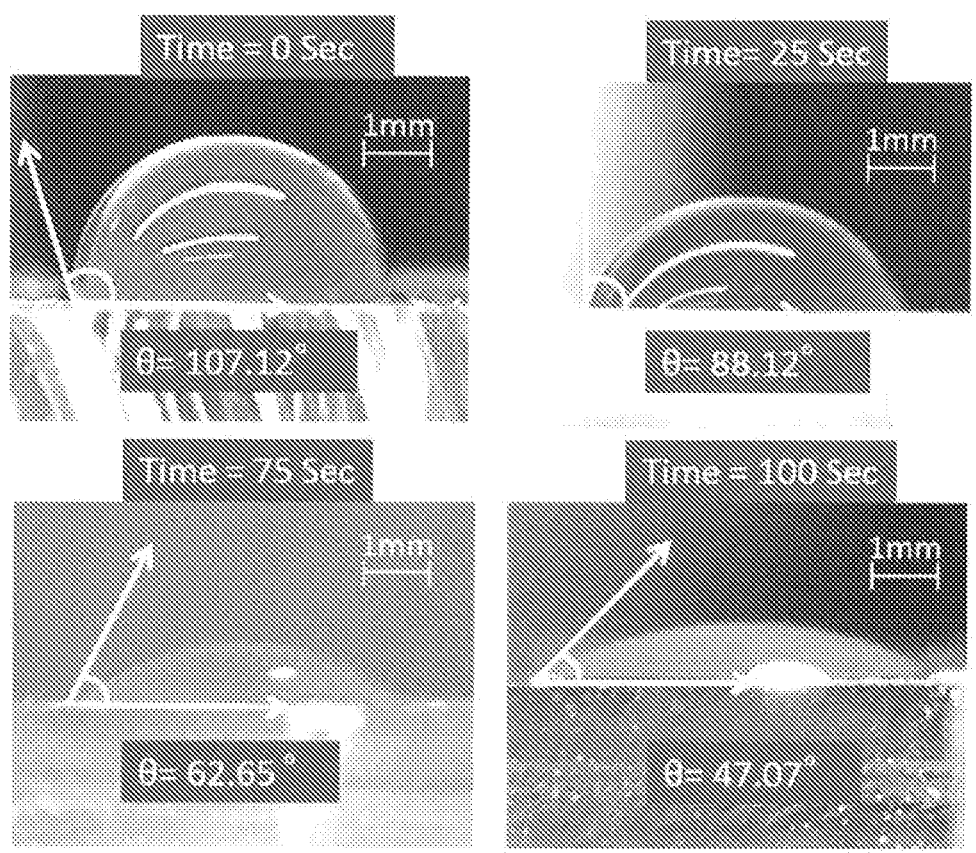
FIG. 21 illustrates an image of Sessile blood drop (4.411 volume) on PDMS surface treated with oxygen plasma for various durations (0 sec, 25 sec, 75 sec, & 100 seconds, respectively)

FIG. 21 shows an image of Sessile blood drop in a PDMS surface treated with oxygen plasma at various time durations. Standard "Image-J" software was used to measure the exact contact angle from the captured images. All the corresponding contact angle measurements were repeated 8 times to check the consistency. The contact angles measured accordingly achieve a precision with an experimental error of ±2° of variation within the theoretical values. Capillary diameter was determined by the below equation (10).

$$\lambda_{blood} = \sqrt{\frac{\gamma_{blood}}{\rho_{blood} g}} \quad (10)$$

According to previously known studies, the surface tension of blood ($\gamma_{blood}$) at 22° C. is 55.89×10−3 N/m [31] and the density of the blood ($\rho_{blood}$) is 1060 kg/m3. The acceleration due to gravity (g) is 9.81 m2/s. The capillary length of blood ($\lambda_{blood}$) is 2.31 mm. The blood drop volume considered is 4.2 ul, (whose radius is 1 mm if the drop shape is assumed as sphere). The diameter of the blood drop sample (which is 2 mm) should be less than the capillary diameter of blood (2.31 mm).

The assumptions made while measuring the contact angle were: [a] The roughness factor of PDMS was ignored, so that the contact angle variations were made just by the surface properties instead of the roughness effect. [b] The values of $\gamma_{blood,air}$, $\gamma_{blood,solid}$ & $\gamma_{solid,air}$ were assumed to be constant throughout the experiment. [c] The surface tension of the blood was higher than the surface tension of the PDMS with surface treatments. [d] The PDMS sample fabricated were rigid, smooth and homogenous. [e] The blood coagulation was not considered and the duration of the experiment is 100 seconds.

The contact angle was varied with the various surface treatments. The contact angle of blood with the PDMS sample had decreased from 107.12° to 47.07° as shown in FIG. 21.

Figure 22:
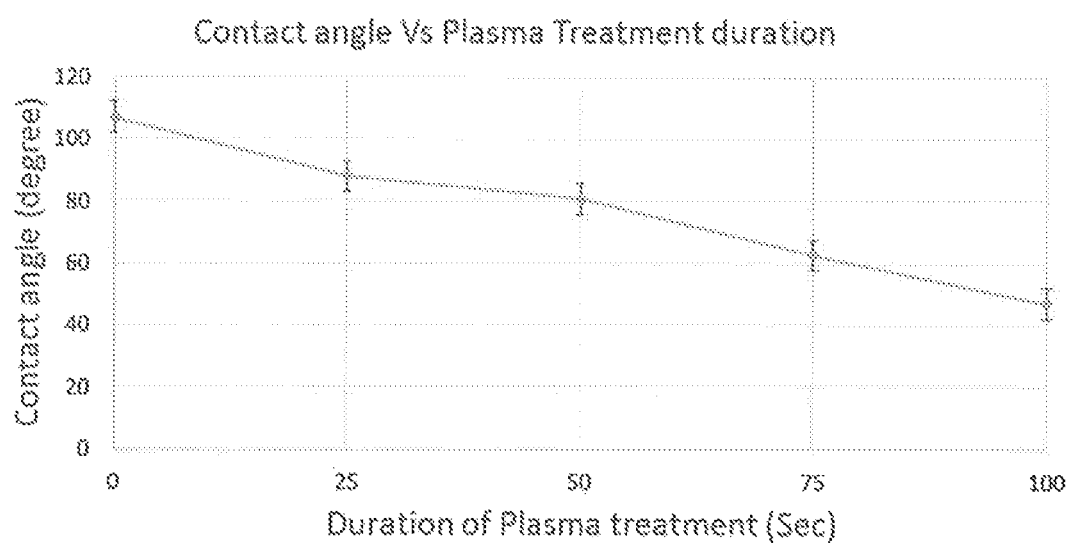
FIG. 22 illustrates a graph of contact angle made by blood drops on PDMS surfaces treated with oxygen plasma for various time durations (0 sec, 25 sec, 75 sec, & 100 sec)

FIG. 22 that illustrates a graph of contact angle. Increase in the duration of oxygen plasma treatment for PDMS samples decreased the contact angle made by blood drop with the PDMS surface. This result implies that the PDMS surface is converted from hydrophobic to hydrophilic with the oxygen plasma treatment.

Figure 23A:
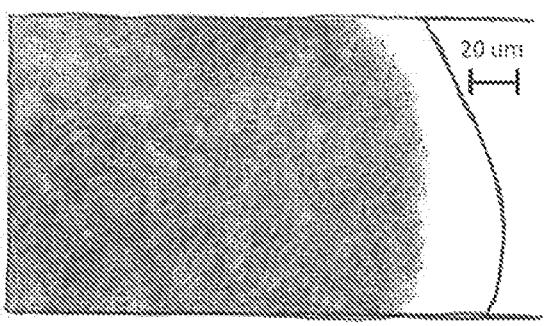
FIGS. 23A and 23B illustrate blood flow in the straight section (Top) and curved section (Bottom) of microchannel of 200 μm width and 107 μm.
Figure 23B:
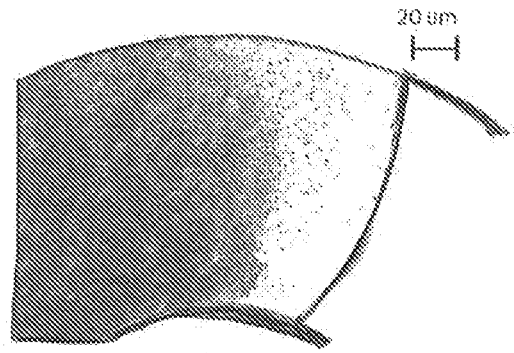
Figure 24:
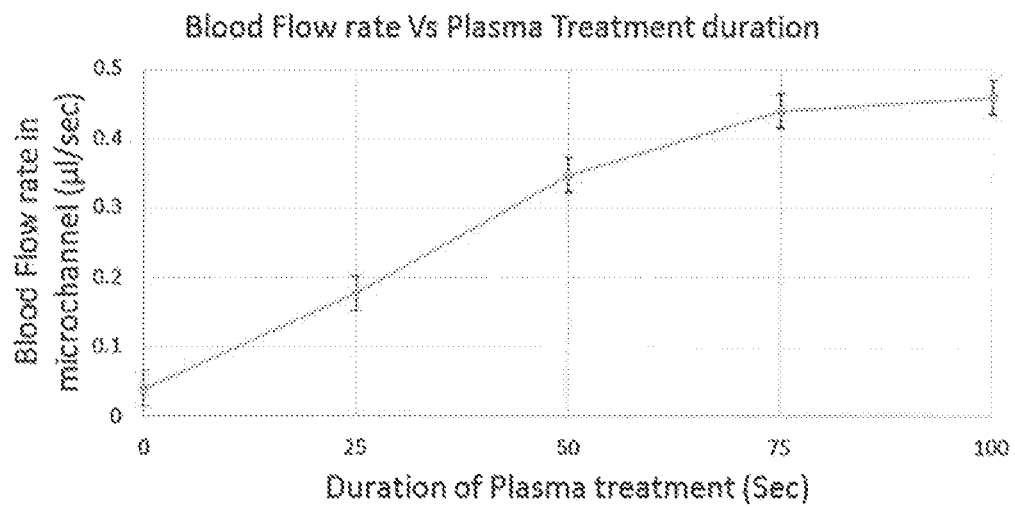
FIG. 24 illustrates a graph of flow rate of the blood in microchannels on PDMS surfaces treated with oxygen plasma for various time durations (0 sec, 25 sec, 75 sec, & 100 sec)

The blood flow in microchannel was due to the capillary effect induced by the surface tension of the blood as shown in FIG. 23A, and FIG. 23B. As the channel surfaces are plasma treated, the contact angle was controlled with the duration of plasma treatment. Since the contact angle controls the capillary effect induced in the blood volume, the duration of plasma treatment can also control the blood flow in the microchannel. So, in the POC biochip the blood flow in microchannels was controlled using the surface treatments without using any external pumps. The images of the blood in straight and curved channels are shown in FIG. 23A, and FIG. 23B. The plot of the blood flow rate in the plasma treated surfaces for various durations is shown in FIG. 24. Shown in FIG. 24 is the graph of flow rate of the body sample, in this example blood, in the microchannels on PDMS surfaces with oxygen plasma for various time durations such as 0 sec., 25 sec., 75 sec. and 100 seconds.

Although this experiment was focused on blood flow control in a POC microchannel to support a biological reaction of antigen and antibody, it is within the scope of this invention to utilize the teachings of this invention with a variation of blood flow at various sections of the microchannel and utilization of the non-permanent effect of plasma treatment (plasma effect sustain for 6 hours at standard air condition and regains its hydrophobic nature). Variation of hydrophobicity of PDMS surface due to exposure in controlled environment after plasma treatment may be utilized in the POC for various beneficial effects on testing, such as separation of components of the sample, among other things.

Figure 25:
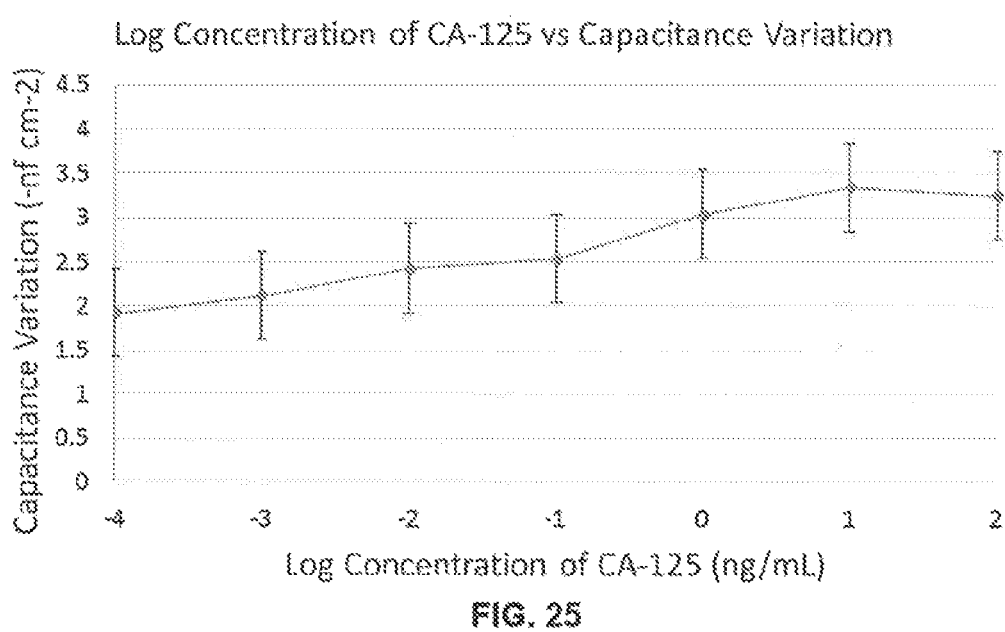
FIG. 25 illustrates a graph of capacitance variation versus logarithm of antigen concentration of CA-125.

The plot of log concentration variation in the analyte generates the change in the capacitance at nano level as shown in FIG. 25. These changes in capacitance confirm the change in the analyte due to the antigen and antibody interaction. The capacitance change was caused due to the formation of antigen and antibody complex formation. The antigen and antibody bond formation provided evidence of cancer antigens (CA-125) existence in the blood sample which helps to diagnose the cancer specific disease in the blood sample.

In one example, the capacitance measurements were made at two stages: Stage-1: During the different layers of biosensor fabrication (like bare electrodes, insulated electrodes with SAM layer, and electrodes with DISEASE ANTIGENS antibodies). Stage-2: During the antigen-antibody interaction 'with' and 'without' microfluidic flow conditions. The electrical measurements in this experiment were measured using the Signatone 2 point probe station and with Agilent 4284A Precision LCR meter. The LCR meter readings were processed using LabVIEW NI 488.2 version software to plot the data. The targeted frequency range was between 10 kHz and 100 kHz with a step of 10 kHz at every succession. Each capacitance measurement was done at 100 mV amplitude with the DC voltage of 0.5V. All the capacitance measurements at corresponding frequency shows the averaged values of three measurements with error bars (the standard deviation of three measurements at each data point) as shown in FIG. 26 and FIG. 27.

Furthermore, the capacitance measurements were performed at the above different stages of the experiment to study the influence of microfluidic flow on the sensing mechanism. The antigen-antibody interaction 'with' and 'without' microfluidic flow of disease antigens on the sensing platform was observed to study the influence of microfluidic flow on sensitivity.

In the first stage, during layer fabrication, capacitance measurements were taken at each modification of the Si-substrate at different layers of the sensing platform.

Figure 26:
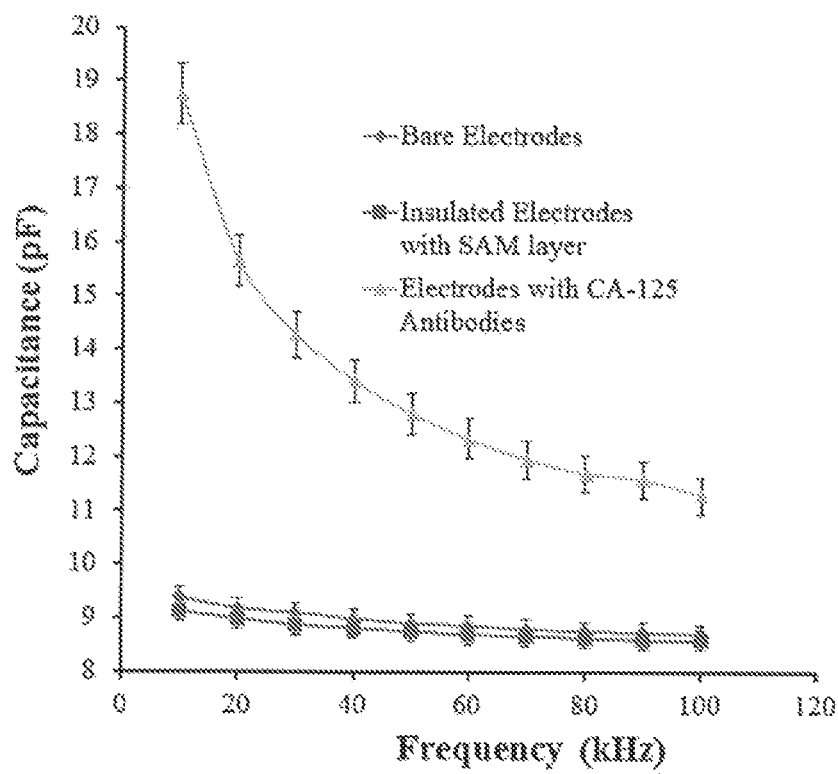
FIG. 26 illustrates a plot of capacitance measurements with frequency for bare electrodes, insulated electrodes with SAM layer, and electrodes with disease antigens.
Figure 27:
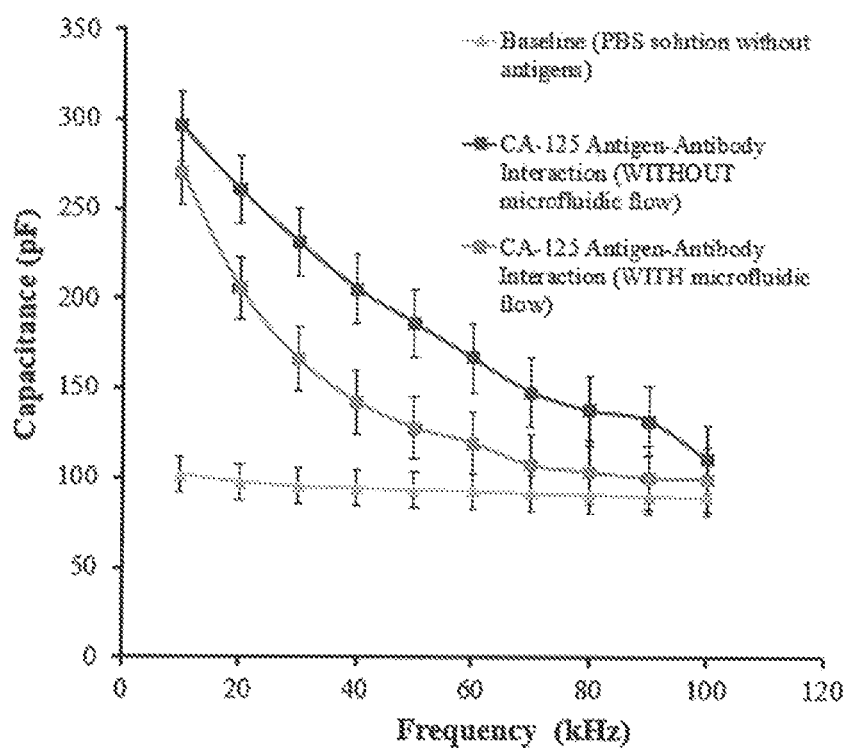
FIG. 27 illustrates plot of capacitance measurements with frequency for baseline (PBS solution without antigens), biofluid sample during microfluidic flow and biofluid sample without microfluidic flow.

FIG. 26 shows the plot of capacitance variation with frequency for bare electrodes, insulated electrodes with SAM layer, and electrodes with immobilized antibodies. The capacitance at the bare electrodes was measured by connecting the probes of electrical analyzer, to the contact pads of the gold nano interdigitated electrodes as 9.12 pF at 10 kHz and 8.59 pF at 100 kHz. Similarly, the capacitance of the insulated electrodes with the SAM layer was measured by connecting the electrical analyzer probes to the contact pads of electrodes coated with SAM layer, as 9.20 pF at 10 kHz and 8.53 pF at 100 kHz. The LCR meter measures the impedance of the net circuit and converts that into capacitance measurement based on the real and imaginary parts of impedance. The higher electron transfer resistance of the SAM layer on the electrodes directly influences the real part of the impedance. The increment in the resistance causes the increment in the net impedance. As a result, the net capacitance of the insulated electrodes with SAM layer has shown lower values when compared to the bare electrode capacitance over the frequency. After the immobilization of the antibodies on the surface activated SAM layer of the electrodes, the capacitance at the immobilized antibodies layer were measured. The measurements were taken by connecting the electrical analyzer probes to the contact pads of the electrodes with immobilized antibodies. The capacitance measurement at the immobilized antibody layer was 18.76 pF at 10 kHz frequency and then reduced to 11.29 pF at 100 kHz frequency as shown in FIG. 26.

During Stage-2, capacitance measurements were made during the Antigen-Antibody interaction 'with' and 'without' microfluidic flow of disease antigens. The capacitance measurements were taken during the antigen-antibody interaction with microchannel and without microchannel. FIG. 27 shows the curves plotted between the capacitance variation and frequency for different conditions such as PBS solution with microfluidic flow, biofluid (antigen in buffer solution) with microfluidic flow and biofluid (antigen in buffer solution) without microfluidic flow.

For the study with a microfluidic flow condition, the sensing platform was enclosed with PDMS microchannel as shown in FIGS. 7D-7F. All fluids (buffer solution and biofluid sample) were passed through the microchannel of same dimensions and at a constant flow rate (0.25 uL/sec) to employ the same microfluidic flow in all the experiments and at all the iterations. As the initial step, the phosphate buffer saline (PBS) solution has been passed through the microchannel and the capacitance measurements were taken during the flow and it is regarded as Baseline. The capacitance values were measured as 101.56 pF at 10 kHz frequency and slowly decreased to 89.45 pF at 100 kHz frequency. It was observed that the capacitance measurements almost remained unchanged over the frequency change In the next step, the biofluid sample (antigens with PBS solution) was passed on the sensing platform with the same microfluidic flow condition. The capacitance measurement in the microfluidic flow condition during antigen-antibody interaction was measured as 270.34 pF at 10 kHz frequency and gradually decreased to 99.58 pF at 100 kHz frequency as shown in FIG. 27.

The disease antigens antigen-antibody interacts are highly selective and specific. The change in the net molecular size due to antigen/antibody complex formation creates a disturbance in the distribution of charges, and creates a dipole moment at the dielectric interface of sensing surface. The hydrocarbon chains present in the proteins are polar in nature. The net charge variation due to the interaction of the hydrocarbons of antibodies and antigens creates a process of local polarization that directly influences the dielectric permittivity of the antigen/antibody complex on the electrode surface. The dipole-dipole interaction stimulates the polarization on the electrode surface. The dielectric of each antigen/antibody complex has unique characteristic over the range of frequencies. Hence when the capacitance measurements during the biofluid sample and the PBS solution (Baseline) in the microfluidic flow conditions were compared, the capacitance measurement at 10 kHz raised from 101.56 pF to 270.34 pF due to the interaction of antigens in the biofluid sample with the immobilized antibodies on the sensing platform.

For the study without microfluidic flow condition, to understand the sensitivity variation due to the microfluidic flow, the biofluid sample with exact same sensing composition (to the microfluidic flow condition) was placed directly as a drop on the sensing platform without using any microchannel and the corresponding capacitance values were measured and compared with the capacitance measurements during the microfluidic flow. The capacitance values when the biofluid sample is placed on the sensing platform at the stationary condition (without microfluidic flow) during the antigen-antibody interaction was measured as 296.09 pF at 10 kHz frequency and then lowered to 110.92 pF at 100 kHz frequency. The capacitance measurement during the antigen-antibody interaction has increased from 270.34 pF to 296.09 pF at 10 kHz when compared between 'with' and 'without' microfluidic flow condition.

The tight confinement of the fluid flow layer in pressure driven microfluidic exert high surface shear stress which can impact the stabilization of the antibodies that are bound to the sensing platform. The shear force applied by the fluid on the surface of the sensing platform in microchannel induces mechanical breakage of the weak bonds of the antibodies with the sensing platform. The breakage in bonds results in the increase in instability of the immobilized antibodies. So due to lack of any shear in 'without microfluidic flow' condition, the stability of the antibody was significantly higher which directly enhanced the sensitivity. Therefore the capacitance measurement of the antigen-antibody interaction is lower in the 'with microfluidic flow' condition when compared to 'without microfluidic flow' condition.

While there has been shown and described various embodiments of the instant invention it is to be appreciated that the invention may be embodied otherwise than is herein specifically shown and described and that, within said embodiments, certain changes may be made in the form and arrangement of the parts without departing from the underlying ideas or principles of this invention as set forth in the claims appended herewith.

What is claimed is:

1. A biochip device for disease diagnostics, comprising:
   a point-of-care (POC) micro biochip having at least one hydrophobic polydimethylsiloxane (PDMS) microchannel having a depth of about 107 µm for flow of at least one source sample of a bodily fluid;
   a hydrophilic surface on the PDMS microchannel by oxygen plasma treatment applied to the microchannels for a duration of 75 seconds to 100 seconds to form a treated microchannel;
   the treated microchannel forming a contact angle between 47.07° to 62.65° for the bodily fluid to have a controlled and an improved capillary flow without use of an external pump device as compared to an untreated microchannel of a similar depth having an untreated contact angle of greater than 100°;
   wherein the hydrophobic surface is not conducent to use with fluid analysis;
   a microfluidic flow condition of the source sample generated by the microchannel;
   the treated microchannel having a spiral pattern to separate the bodily fluid and allow different concentrations of the bodily fluid at each section of the biochip;
   a plurality of metallic nano interdigitated electrodes (IDE) disposed within the treated microchannel for at least providing enhanced sensitivity detection of a disease state, and the electrodes having at least one type of antibody disposed thereon;
   a nano circuit incorporated in the biochip wherein a disease-specific antigen from the sample forms an antigen-antibody complex interaction that affects capacitance detected via an electrical change in the nano circuit; and
   wherein the flow of the bodily fluid and time allowed for the antigen-antibody complex interaction are controllable by controlling the contact angle of the bodily fluid; and a resulting analyte with the micro fluidic flow is more detectable than without the micro fluidic flow.

2. The device of claim 1, wherein the treated microchannel is designed to include non-optical sensing mechanisms and electrical sensing with no micro pumps required to inject the sample of the bodily fluid.

3. The device of claim 2, wherein the spiral pattern further includes multiple channels that are connected to a same inlet through which the sample flows for detecting different disease antigens from the same sample at the same time.

4. The device of claim 1, wherein at least a part of the treated microchannel is made of bio-compatible materials.

5. The device of claim 1 wherein the bodily fluid is a blood sample and the micro biochip provides a disease antigen information on existence of specific disease antigens in the blood sample from a finger prick; and capacitances are measured at two stages in the micro biochip, wherein a first stage (stage-1) capacitance is measured before the antigen and antibody complex formation and wherein a second stage (stage-2) capacitance is measure after the antigen and antibody complex formation; and a difference in capacitance between stage-2 capacitance and stage-1 capacitance provides the information about existing disease antigen in the bio fluid.

6. The device of claim 1 wherein the electrodes are selected from a group consisting of (a) transition metals including gold, silver, platinum, iron, copper, cobalt, (b) alkali or alkaline metals including lithium, and magnesium, (c) semimetals including silicon, and germanium, (d) conductive non-metals including carbon and any combination thereof.

7. The device of claim 1 wherein the electrical change in the nano circuit has a capacitance of 270.34 picofarads (pF).

8. The device of claim 1 wherein a non-microfluidic flow condition of the source sample is generated and the electrical change in the nano circuit has a difference in capacitance of 296.09 picofarads (pF).

9. The device of claim 1 wherein the electrical change and capacitive sensitivity variation of the micro biochip is lower in a microfluidic flow condition of the sample than without the microfluidic flow condition; and the treated microchannels is about 2.31 mm in length.

10. A method of using a biochip device for disease diagnostics, comprising
    providing a point-of care (POC) microbiochip, the microchip including:
    at least one hydrophobic polydimethylsiloxane (PDMS) microchannel having a depth of about 107µm for flow of at least one source sample of a bodily fluid;
    a hydrophilic surface on the PDMS microchannel by oxygen plasma treatment applied to the microchannels for a duration of 75 seconds to 100 seconds to form a treated microchannel;
    the treated microchannel forming a contact angle between 47.07° to 62.65° for the bodily fluid to have a controlled and improved capillary flow without use of an external pump device as compared to an untreated microchannel of a similar depth having an untreated contact angle of greater than 100°;
    wherein the hydrophobic surface is not conducent to use with fluid analysis;
    a microfluidic flow condition of the source sample generated by the microchannel;
    the treated microchannel having a spiral pattern to separate the bodily fluid and allow different concentrations of the bodily fluid at each section of the biochip;
    a plurality of metallic nano interdigitated electrodes (IDE) disposed within the treated microchannel for at least providing enhanced sensitivity detection of a disease state, and the electrodes having at least one type of antibody disposed thereon;

a nano circuit incorporated in the biochip wherein a disease-specific antigen from the sample forms an antigen-antibody complex interaction that affects capacitance detected via an electrical change in the nano circuit; and wherein the flow of the bodily fluid and time allowed for the antigen-antibody complex interaction are controllable by controlling the contact angle of the bodily fluid; and a resulting analyte with the micro fluidic flow is more detectable than without the micro fluidic flow;

applying only a single amount of a bodily fluid sample to a micro biochip; and allowing sample flow that is self-driven and controlled through the at least one treated microchannel disposed in the micro bio chip, the microchannel having at least one biomarker immobilized on a multiple amount of metallic electrodes in communication with the microchannel; and wherein disease-specific antigens from the sample form the antigen-antibody complex interaction that affects electrical properties; and the antigen-antibody interaction is detected via an electrical change in a nano circuit incorporated in the biochip.

11. The method of claim 10, wherein the electrical change includes a change in an electrical property selected from the group consisting of impedance, capacitance, resistance, voltage, current, and any combination thereof.

12. The method of claim 10, further includes obtaining diagnostic results of at least one disease state.

13. The method of claim 10 further includes drawing the sample from a finger prick.

14. The method of claim 10, wherein the treated micro channel is about 2.31 mm in length.

15. The method of claim 10, wherein a non-microfluidic flow condition of the source sample is generated.

16. A method for disease diagnostics, comprising:

preparing a sample for deposit into a biochip, wherein the biochip includes:

providing a point-of-care (POC) micro biochip having at least one hydrophobic polydimethylsiloxane (PDMS) microchannel having a depth of about 107μm for flow of at least one source sample of a bodily fluid;

a hydrophilic surface on the PDMS microchannel by oxygen plasma treatment applied to the microchannels for a duration of 75 seconds to 100 seconds to form a treated microchannel;

the treated microchannel forming a contact angle between 47.07° to 62.65° for the bodily fluid to have a controlled and improved capillary flow without use of an external device as compared to an untreated microchannel of a similar depth having an untreated contact angle greater than 100°;

wherein the hydrophobic surface is not conducent to use with fluid analysis;

a microfluidic flow condition of the source sample generated by the microchannel;

the treated microchannel having a spiral pattern to separate the bodily fluid and allow different concentrations of the bodily fluid at each section of the biochip;

a plurality of metallic nano interdigitated electrodes (IDE) disposed within the treated microchannel for at least providing enhanced sensitivity detection of a disease state, and the electrodes having at least one type of antibody disposed thereon;

a nano circuit incorporated in the biochip wherein a disease-specific antigen from the sample forms an antigen-antibody complex interaction that affects capacitance detected via an electrical change in the nano circuit;

wherein the flow of the bodily fluid and time allowed for the antigen-antibody complex interaction are controllable by controlling the contact angle of the bodily fluid; and a resulting analyte with the micro fluidic flow is more detectable than without the micro fluidic flow;

depositing the sample into the inlet of the biochip, causing the sample to advance through the treated microchannel; and analyzing the sample based on the interaction between the sample and the nano interdigitated electrodes.

17. The method of claim 16, wherein the biomarker coating of the nano interdigitated electrodes is adapted to detect at least one antigen or antibody.

18. A point-of-care (POC) micro biochip for disease diagnostics, comprising:

a biocompatible polymer mold including at least one microchannel, each microchannel extending from an inlet on the mold to an outlet on the mold the microchannel is a hydrophobic polydimethylsiloxane (PDMS) microchannel having a depth of about 107 μm for flow of at least one source sample of a bodily fluid;

a hydrophilic surface on the PDMS microchannel by oxygen plasma treatment applied to the microchannels for a duration of 75 seconds to 100 seconds to form a treated microchannel;

the treated microchannel forming a contact angle between 47.07° to 62.65° for the bodily fluid to have a controlled and improved capillary flow without use of an external device as compared to an untreated microchannel of a similar depth having an untreated contact angle greater than 100°;

wherein the hydrophobic surface is not conducent to use with fluid analysis;

a microfluidic flow condition of the source sample generated by the microchannel;

the treated microchannel having a spiral pattern to separate the bodily fluid and allow different concentrations of the bodily fluid at each section of the biochip;

two conductive nano interdigitated metallic electrodes each coated with a unique biomarker, the conductive nano interdigitated electrodes in communication with the microchannel at separate locations within the treated microchannel for at least providing enhanced sensitivity detection of a disease state, and the electrodes having at least one type of antibody disposed thereon; and two contact pads for each conductive nano interdigitated electrode to transmit electrical measurements to an external device;

a nano circuit incorporated in the biochip wherein a disease-specific antigen from the sample forms an antigen-antibody complex interaction that affects capacitance detected via an electrical change in the nano circuit; and wherein the flow of the bodily fluid and time allowed for the antigen-antibody complex interaction are controllable by controlling the contact angle of the bodily fluid; and a resulting analyte with the micro fluidic flow is more detectable than without the micro fluidic flow.

19. The biochip of claim 18, wherein the metallic electrodes contain gold.

20. The biochip of claim 18, wherein the biocompatible polymer mold is made at least in part of a biocompatible material including polydimethylsiloxane, and the biochip has a self-assembled monolayer (SAM) to provide insulation and adhesion on the metallic electrodes.

\* \* \* \* \*